(12) United States Patent
Okamoto et al.

(10) Patent No.: US 12,324,878 B2
(45) Date of Patent: Jun. 10, 2025

(54) MEDICAL DEVICE AND METHOD OF MANUFACTURING THE SAME

(71) Applicant: Nikkiso Company Limited, Tokyo (JP)

(72) Inventors: Shingo Okamoto, Shizuoka (JP); Kosei Nishida, Shizuoka (JP); Kazuhide Ono, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 924 days.

(21) Appl. No.: 17/128,668

(22) Filed: Dec. 21, 2020

(65) Prior Publication Data

US 2021/0106744 A1  Apr. 15, 2021

Related U.S. Application Data

(63) Continuation of application No. PCT/JP2019/024655, filed on Jun. 21, 2019.

(30) Foreign Application Priority Data

Jun. 22, 2018 (JP) .................................. 2018-119262

(51) Int. Cl.
*A61M 1/36* (2006.01)
*G01L 7/08* (2006.01)

(52) U.S. Cl.
CPC .............. *A61M 1/3601* (2014.02); *G01L 7/08* (2013.01); *A61M 2205/3331* (2013.01); *A61M 2205/75* (2013.01); *A61M 2207/10* (2013.01)

(58) Field of Classification Search
CPC .............. A61M 1/3601; A61M 1/3641; A61M 2205/3331; A61M 2205/75;
(Continued)

(56) References Cited

U.S. PATENT DOCUMENTS 4,457,050 A * 7/1984 Kanzaka ................. A44B 1/34
   24/453
4,801,125 A  1/1989 Kocher
(Continued)

FOREIGN PATENT DOCUMENTS

DE   102008034920 A1  9/2009
EP       0074733 A1  3/1983
(Continued)

OTHER PUBLICATIONS

European Search Report for Application No. 19822411.5, dated May 31, 2022, 10 pgs.
(Continued)

*Primary Examiner* — John Fitzgerald
*Assistant Examiner* — Truong D Phan
(74) *Attorney, Agent, or Firm* — Young Basile Hanlon & MacFarlane, P.C.

(57) ABSTRACT

A medical device includes a case obtained by mating a liquid-phase-portion case and a gas-phase-portion case to each other, a membrane member as an elastic member with which a liquid-phase portion covered by the liquid-phase-portion case and a gas-phase portion covered by the gas-phase-portion case are separated from each other, fixing parts and at which the liquid-phase-portion case and the gas-phase-portion case that are mated to each other are fixed to each other, holding surfaces and between which a peripheral edge of the membrane member is held, and a sealing part that seals the entirety of the peripheral edge of the membrane member held between the holding surfaces and. The medical device has a releasing part that releases the pressure in an air gap produced between the sealing part and the fixing parts.

5 Claims, 23 Drawing Sheets

(58) Field of Classification Search
CPC .......... A61M 2207/00; A61M 2207/10; A61M 60/109; A61M 60/268; A61M 60/279; A61M 60/37; A61M 60/851; A61M 1/3639; A61M 1/14; A61M 5/36; A61M 1/966; A61M 2025/0001; A61M 2025/0002; A61M 60/523; A61M 60/531; G01L 19/0023; G01L 19/0046; G01L 7/08; G01L 13/025; G01L 7/082; G01L 9/0016
USPC .............................................. 73/861.47, 715
See application file for complete search history.

(56) References Cited

U.S. PATENT DOCUMENTS

| | | | |
|---|---|---|---|
| 4,908,493 | A | 3/1990 | Susemihl |
| 5,221,271 | A | 6/1993 | Nicholson et al. |
| 6,392,208 | B1 | 5/2002 | Arx |
| 8,092,414 | B2 | 1/2012 | Schnell et al. |
| 8,960,010 | B1 | 2/2015 | Crnkovich et al. |
| 10,775,252 | B2 | 9/2020 | Funamura et al. |
| 2003/0115965 | A1 | 6/2003 | Mittelstein et al. |
| 2006/0063462 | A1* | 3/2006 | Ding ..................... B81B 7/0038 445/24 |
| 2007/0118153 | A1 | 5/2007 | Funamura et al. |
| 2007/0295093 | A1 | 12/2007 | Reiter et al. |
| 2009/0071258 | A1 | 3/2009 | Kouda et al. |
| 2013/0089802 | A1* | 4/2013 | Artibise .............. H01M 8/2483 429/535 |
| 2016/0089484 | A1 | 3/2016 | Lindley et al. |
| 2017/0312412 | A1 | 11/2017 | Mochizuki |
| 2017/0340798 | A1 | 11/2017 | Lindley et al. |
| 2018/0093033 | A1* | 4/2018 | Crnkovich .......... A61M 1/3639 |
| 2020/0198459 | A1 | 6/2020 | Bouffier et al. |
| 2021/0106744 | A1 | 4/2021 | Okamoto et al. |

FOREIGN PATENT DOCUMENTS

| | | |
|---|---|---|
| EP | 0330891 A1 | 9/1989 |
| EP | 1843140 A2 | 10/2007 |
| EP | 2155287 A1 | 2/2010 |
| EP | 2692373 A1 | 2/2014 |
| EP | 2155287 B1 | 10/2017 |
| JP | S62-051630 B2 | 10/1987 |
| JP | H02-001275 A | 1/1990 |
| JP | H09-024026 A | 1/1997 |
| JP | 2008-051663 A | 3/2008 |
| JP | 2008-136673 A | 6/2008 |
| JP | 2010-172739 A | 8/2010 |
| JP | 2014-204779 A | 10/2014 |
| JP | 2015-112223 A | 6/2015 |
| JP | 2016-221028 A | 12/2016 |
| JP | 2017-106812 A | 6/2017 |
| JP | 2019-063439 A | 4/2019 |
| WO | 2007/040223 A1 | 4/2007 |
| WO | 2007/120812 A2 | 10/2007 |
| WO | 2008/106191 A2 | 9/2008 |
| WO | 2014/028103 A1 | 2/2014 |
| WO | 2014/093846 A1 | 6/2014 |
| WO | 2015/099932 A1 | 7/2015 |
| WO | 2017/015322 A1 | 1/2017 |
| WO | 2019221202 A1 | 11/2019 |
| WO | 2019221203 A1 | 11/2019 |
| WO | 2019221204 A1 | 11/2019 |
| WO | 2019221205 A1 | 11/2019 |

OTHER PUBLICATIONS

International Search Report dated Jul. 16, 2019 for Application No. PCT/JP2019/024655 published as WO2019/245017.
International Search Report dated Jun. 11, 2019 for Application No. PCT/JP2019/019393 published as WO2019221202.
Potentially related U.S. Appl. No. 17/093,821, filed Nov. 10, 2020 entitled "Pressure Detector," Published as WO2019221203.
Potentially related U.S. Appl. No. 17/093,823, filed Nov. 10, 2020 entitled "Pressure Detector," Published as WO2019221204.
Potentially related U.S. Appl. No. 17/093,825, filed Nov. 10, 2020 entitled "Pressure Detector," Published as WO2019221205.
Potentially related U.S. Appl. No. 17/093,817, filed Nov. 10, 2020 entitled "Pressure Detector," Published as WO2019221202.
Potentially related U.S. Appl. No. 17/128,705, filed Dec. 21, 2020 entitled "Method and Apparatus of Manufacturing Medical Device".

* cited by examiner

[Fig. 1]
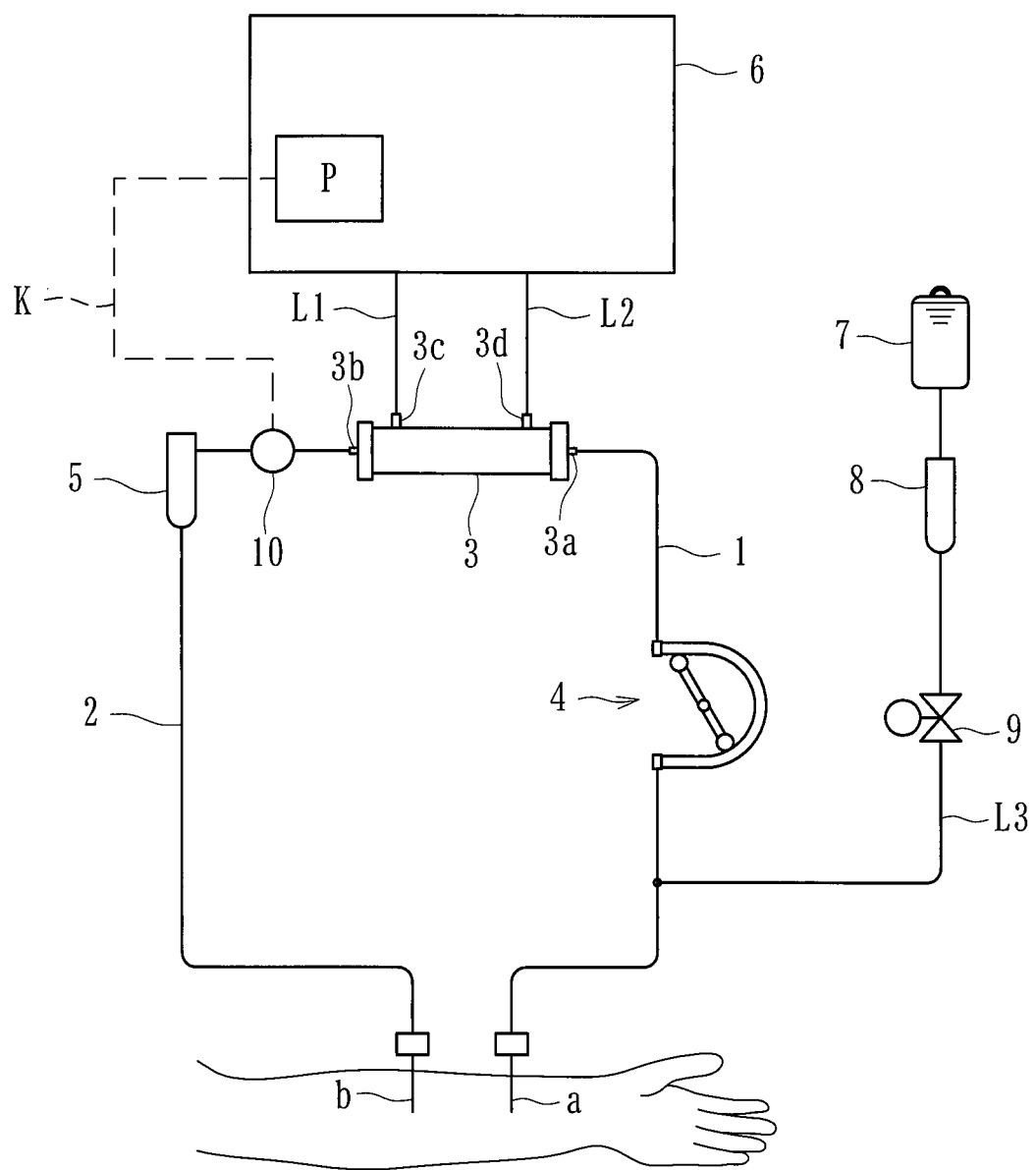

[Fig. 2]
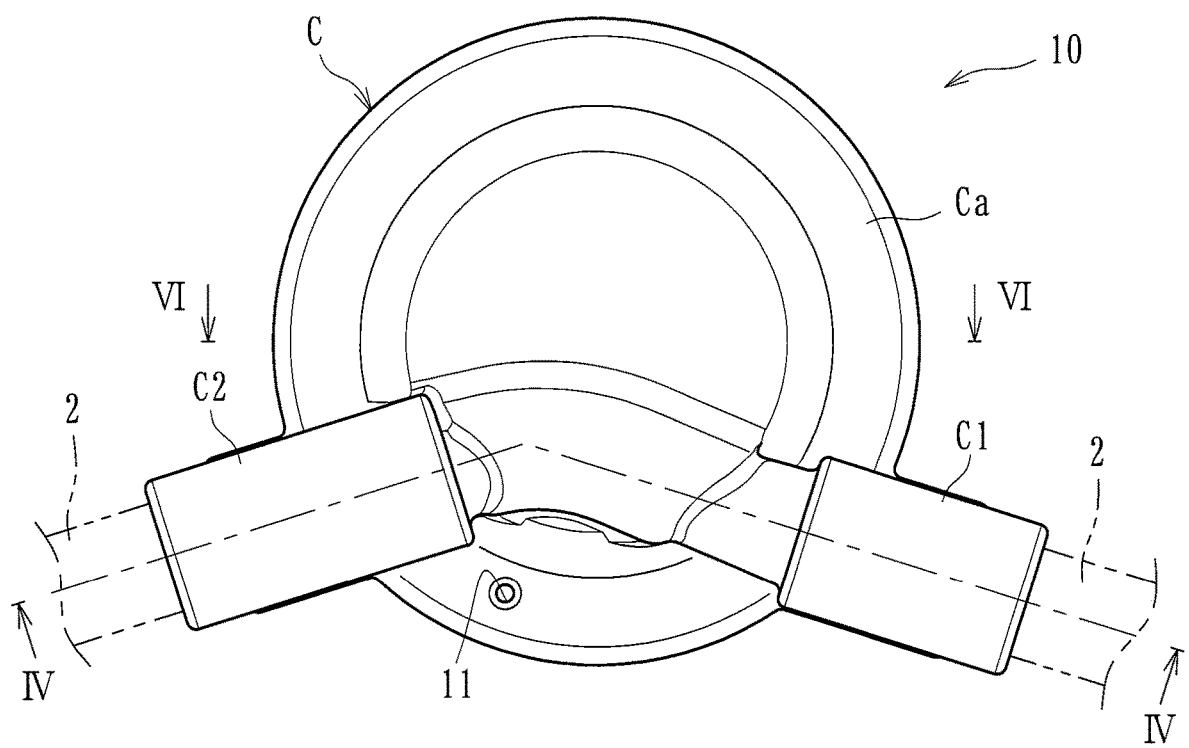
[Fig. 3]
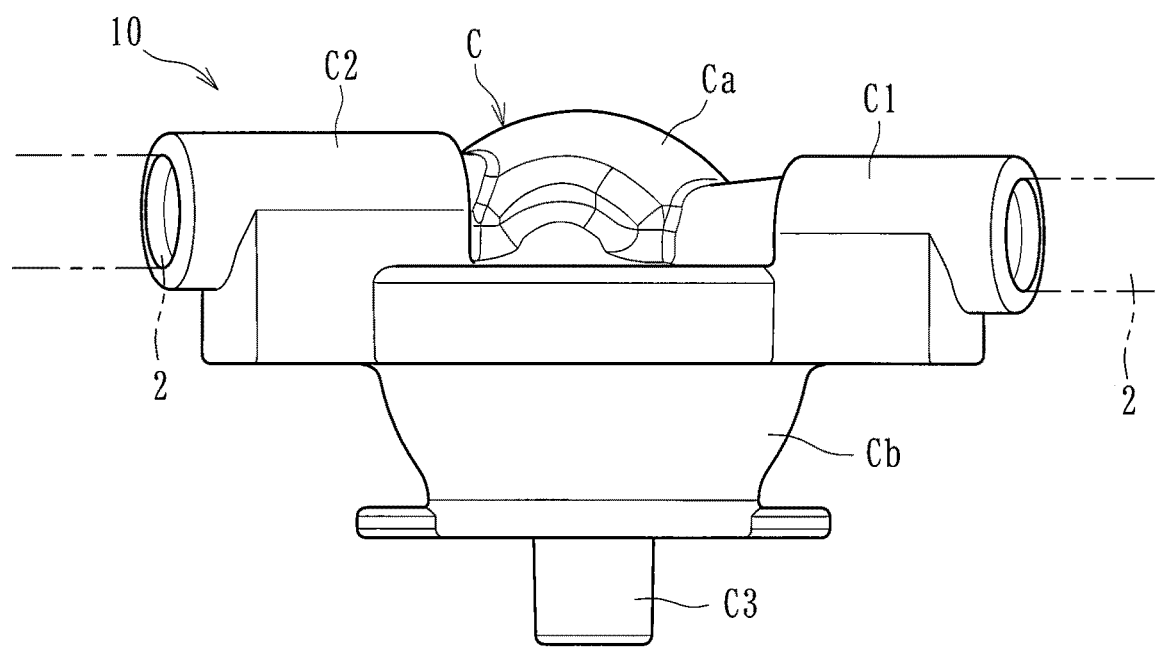

[Fig. 4]
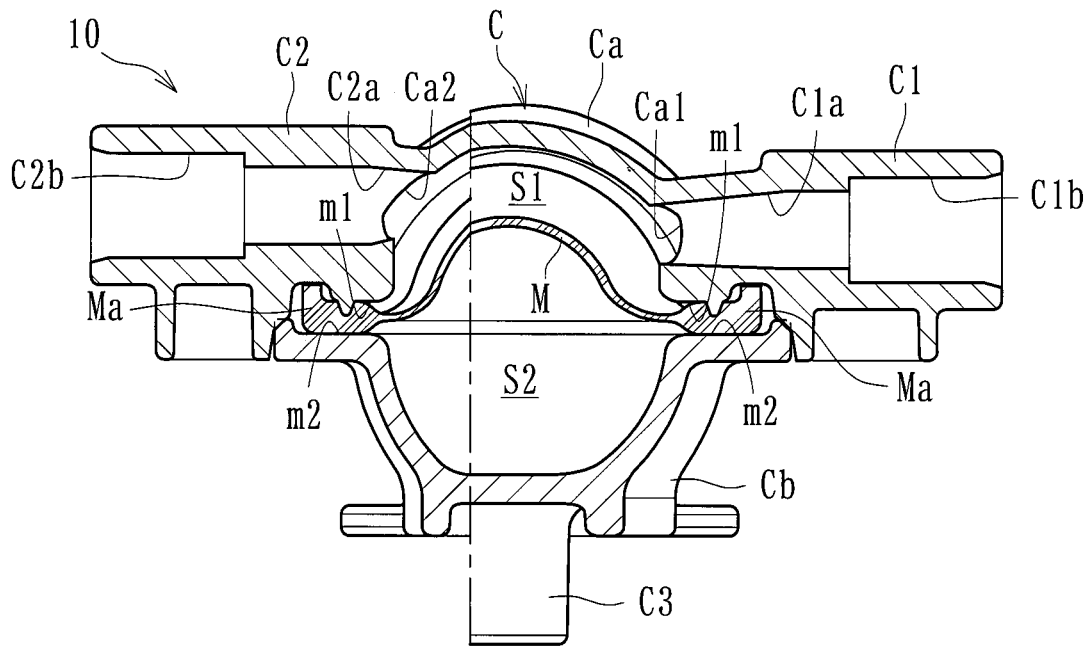
[Fig. 5]
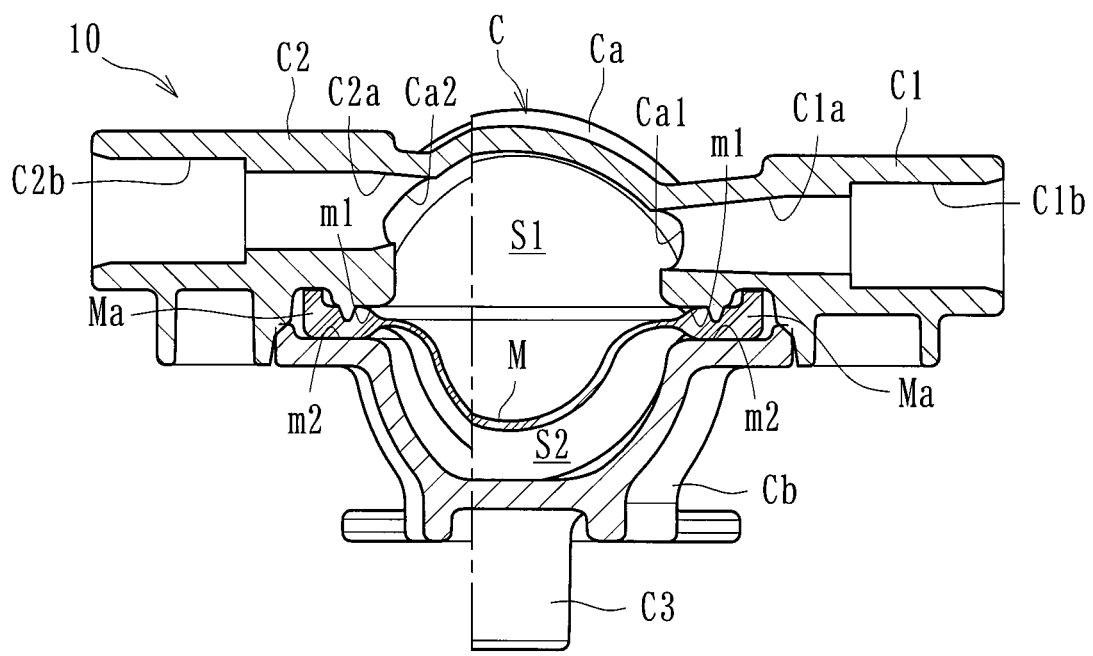

[Fig. 6]
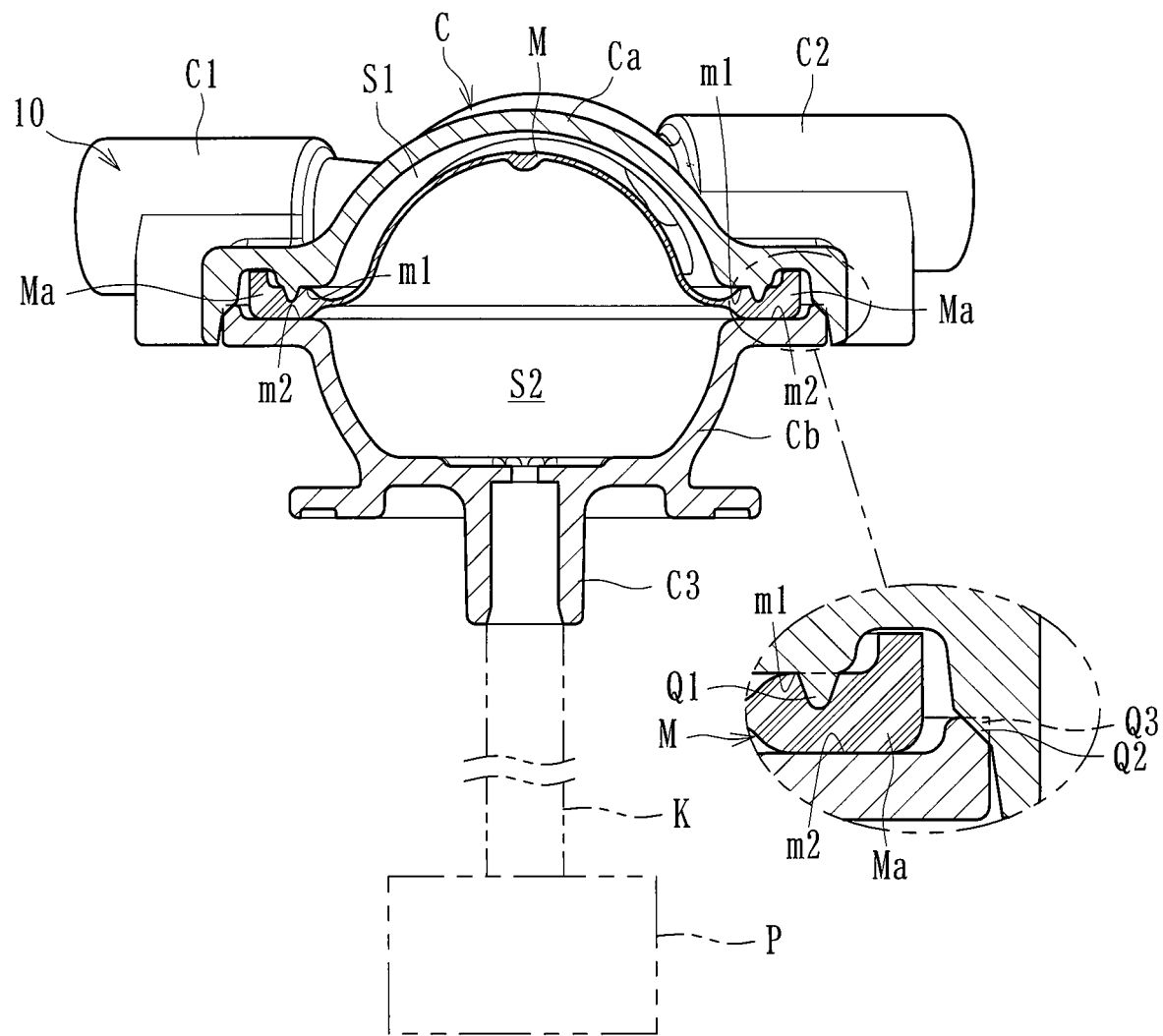

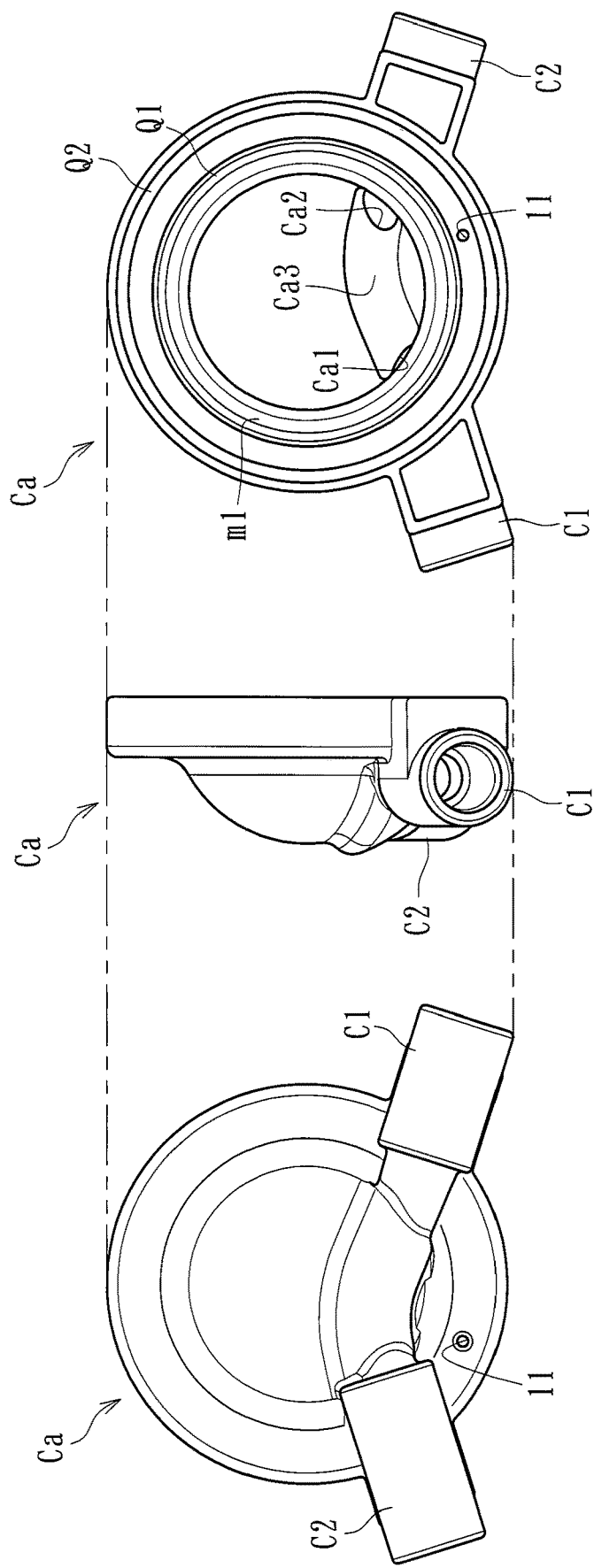
[Fig. 7]

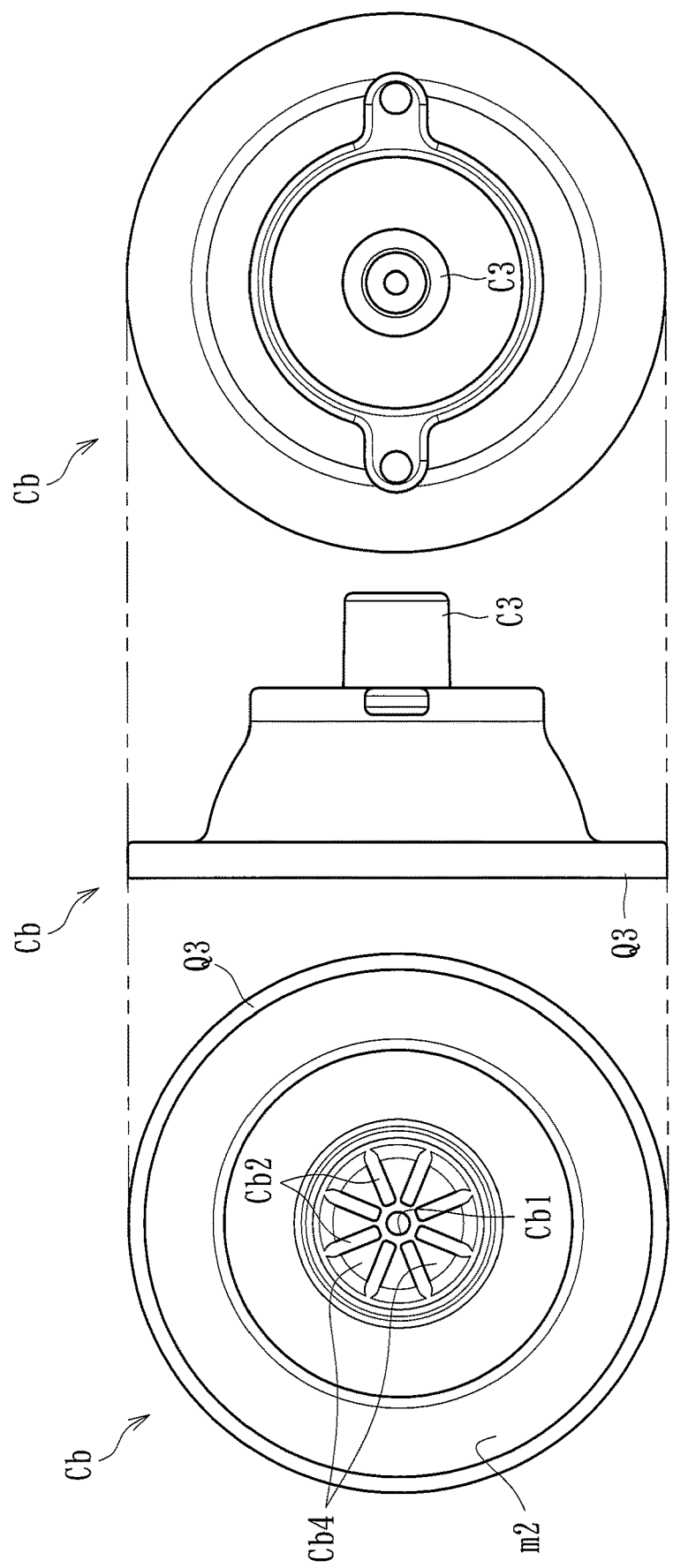
[ Fig. 8 ]

[Fig. 9]
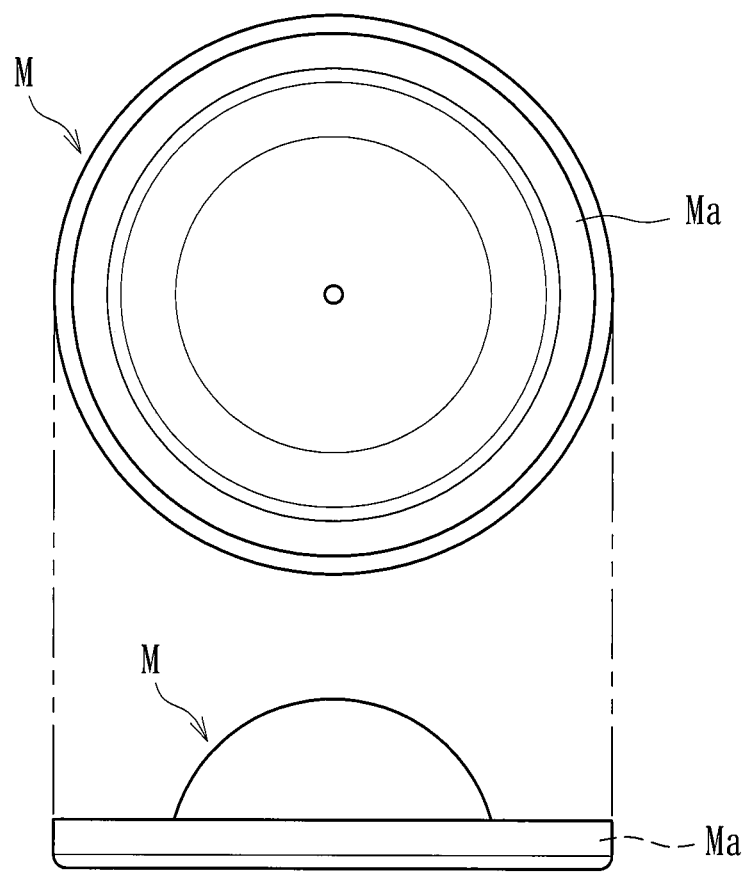

[ Fig. 10 ]
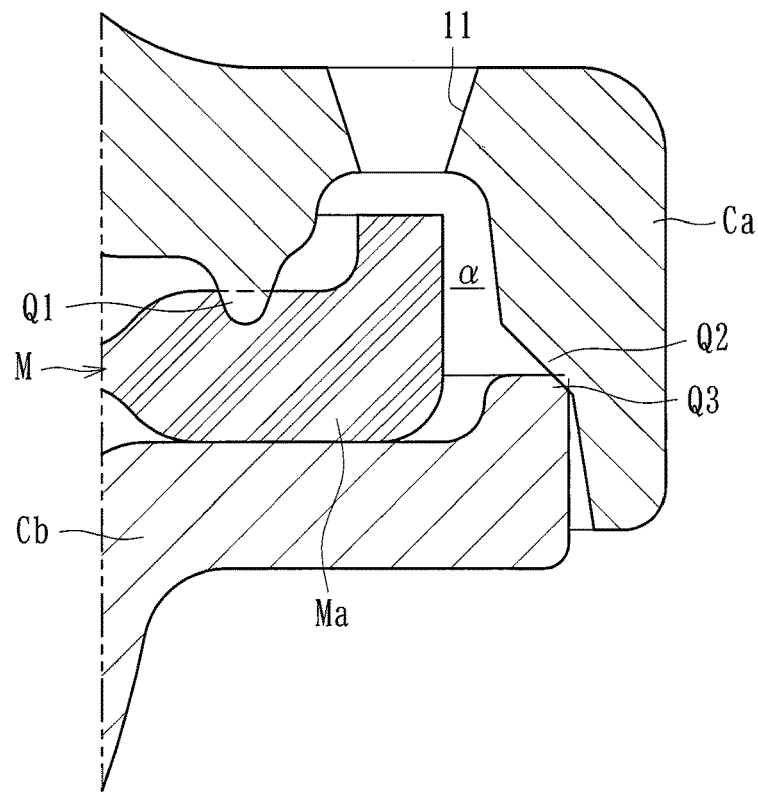
[ Fig. 11 ]
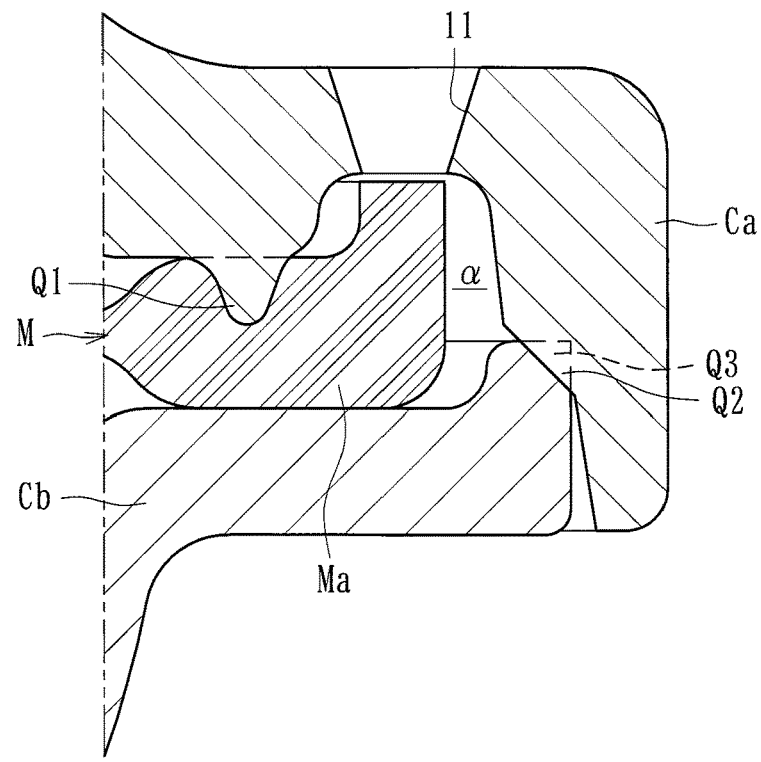

[Fig. 12]
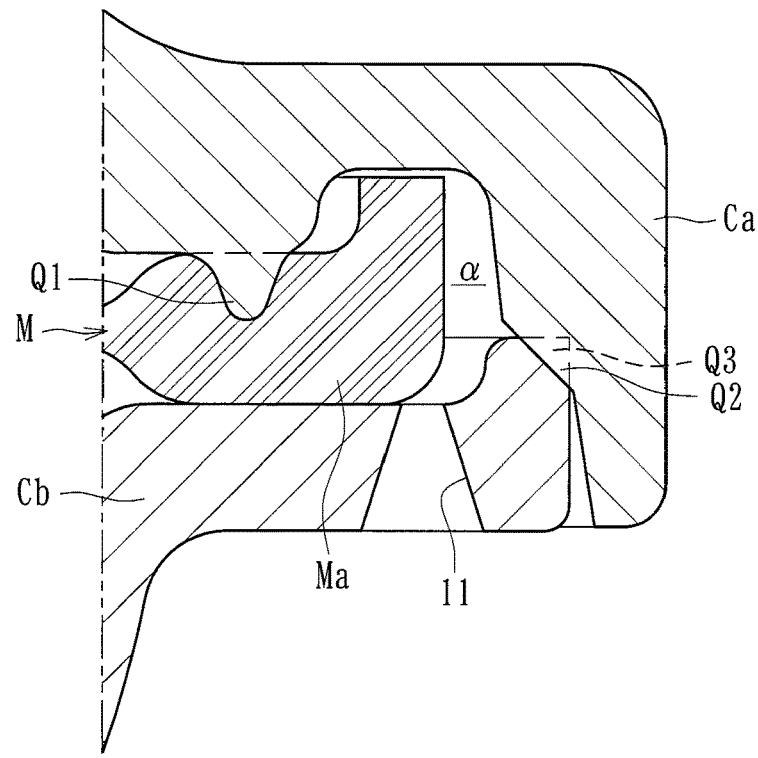
[Fig. 13]
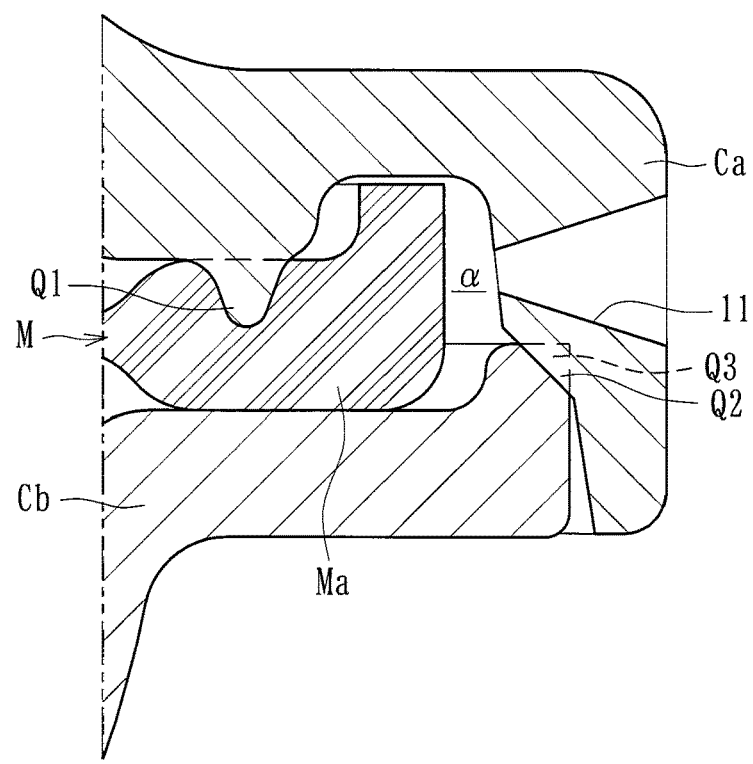

[ Fig. 14 ]
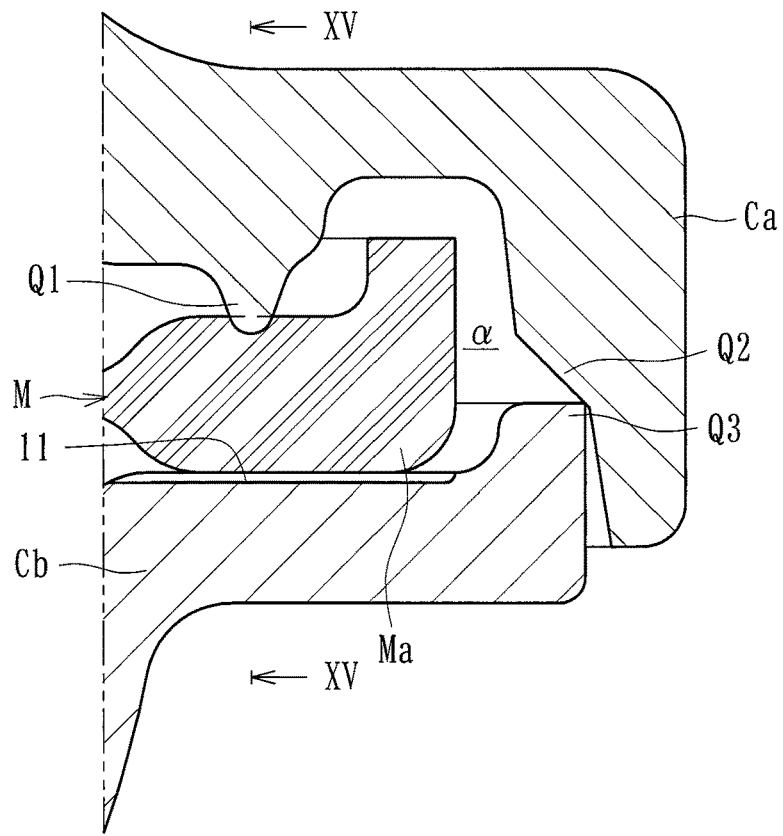
[ Fig. 15 ]
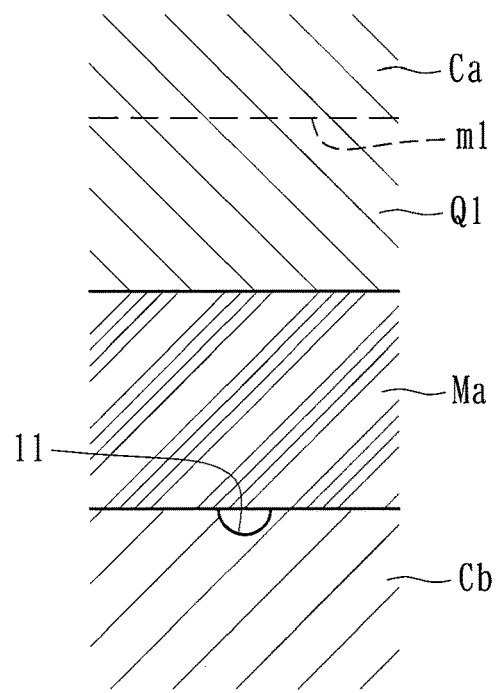

[Fig. 16]
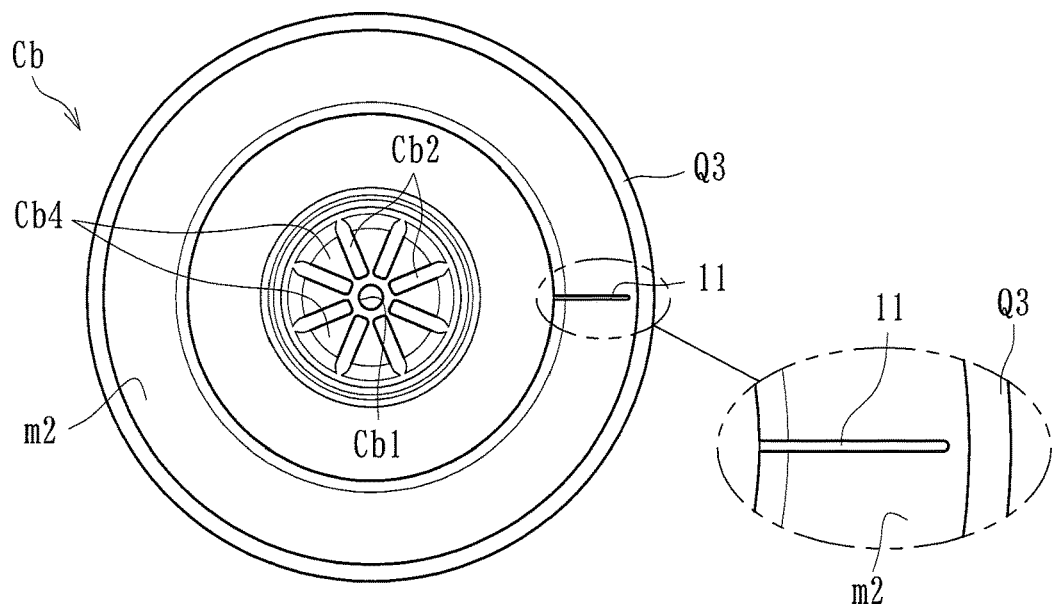
[Fig. 17]
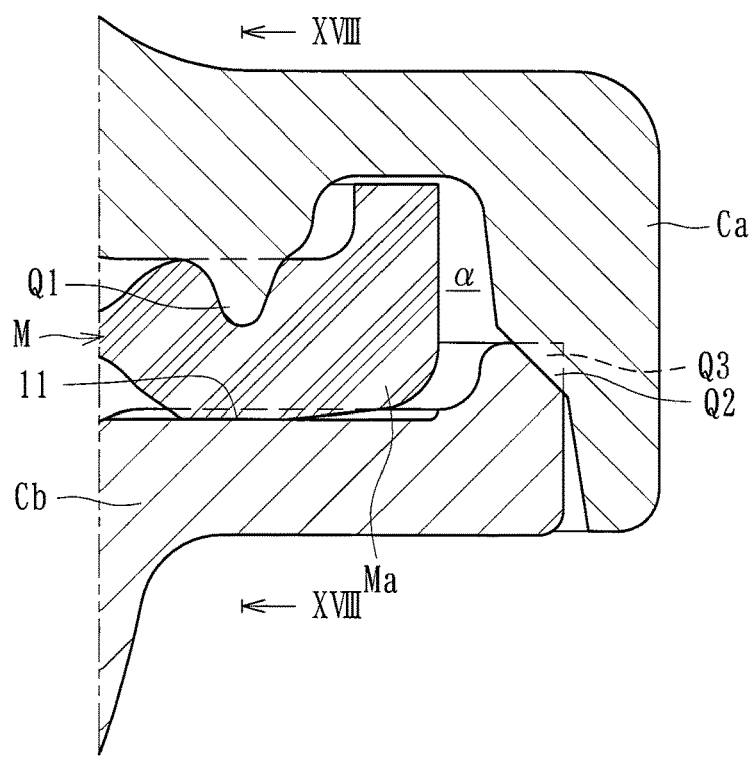

[Fig. 18]
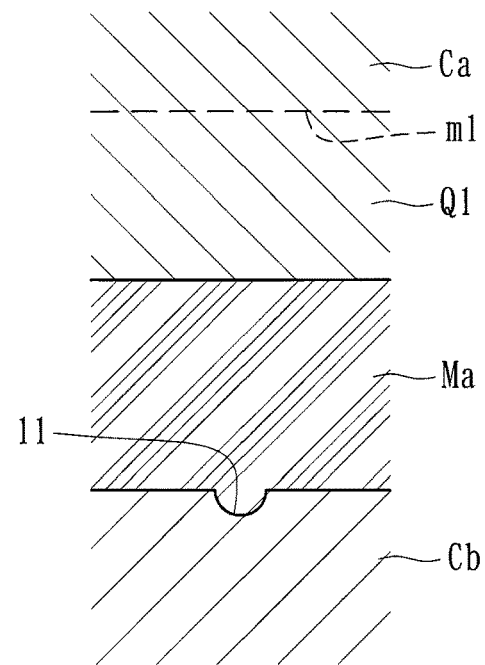
[Fig. 19]
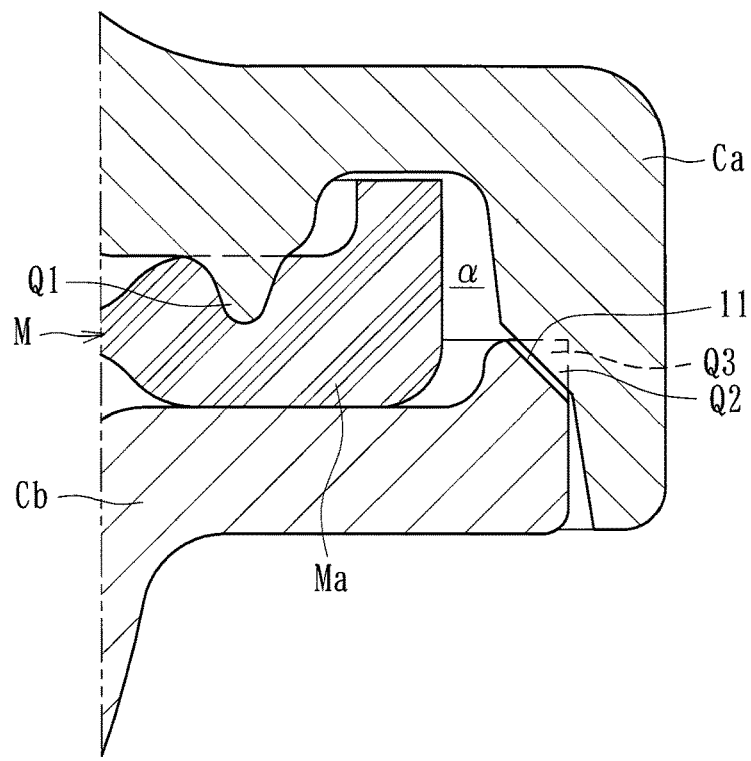

[Fig. 20]
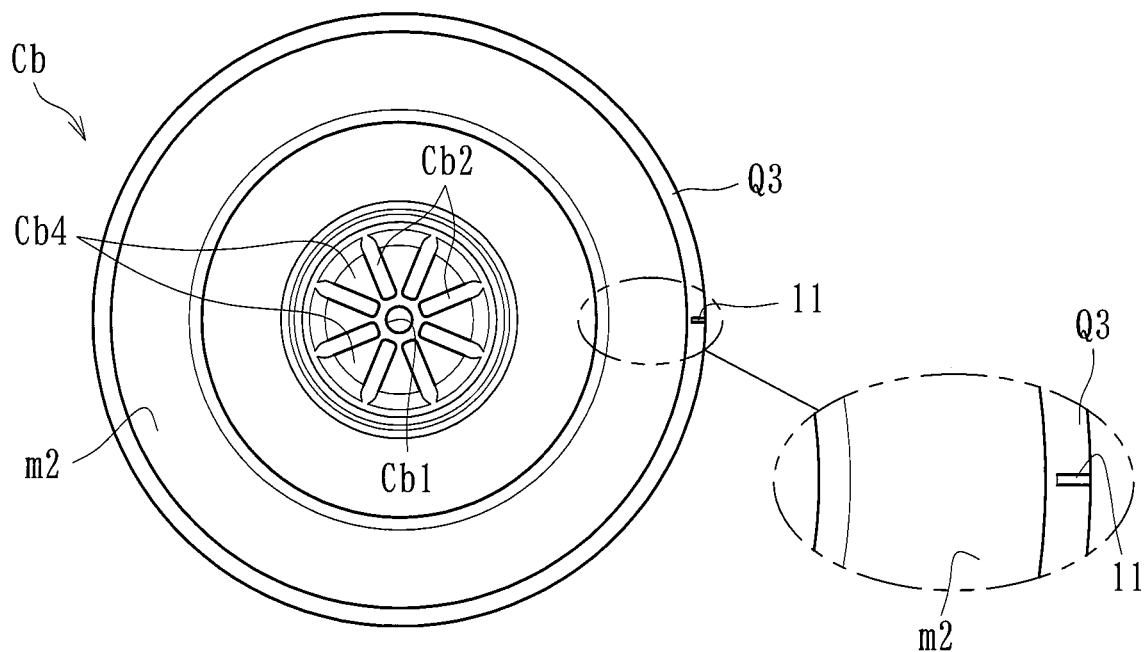
[Fig. 21]
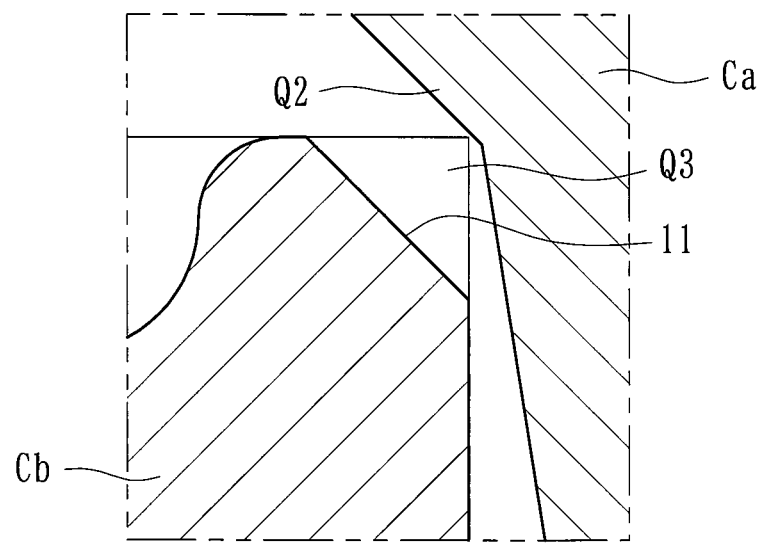

[ Fig. 22 ]
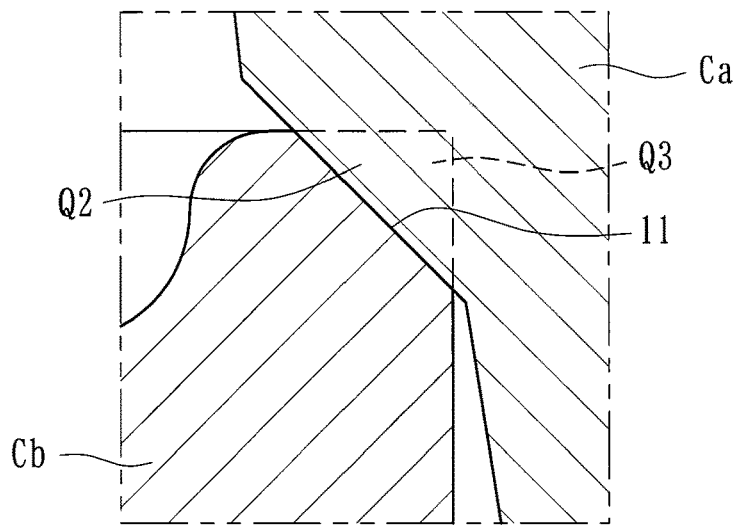
[ Fig. 23 ]
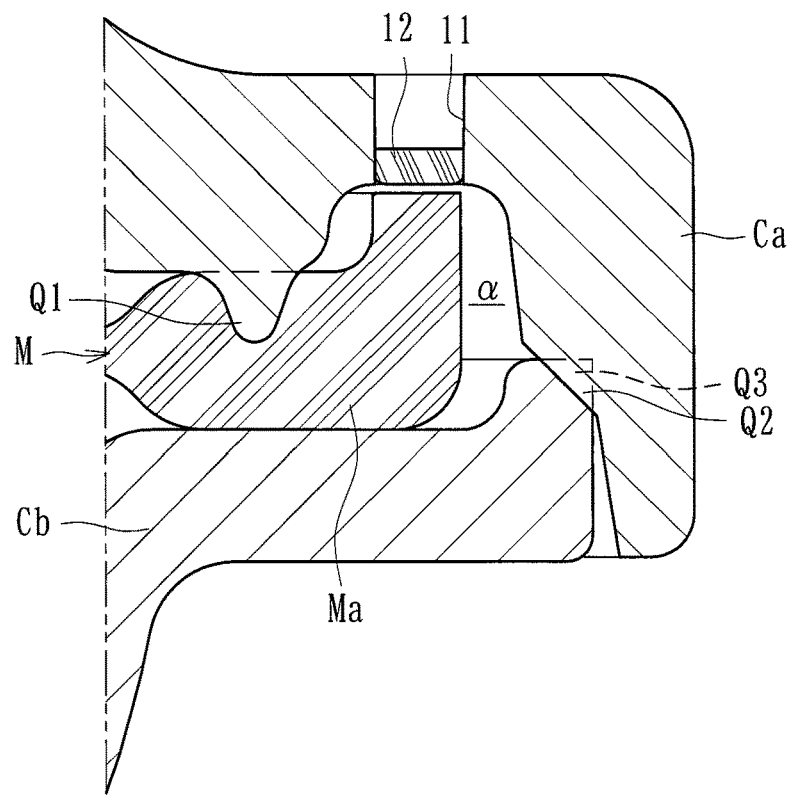

[Fig. 24]
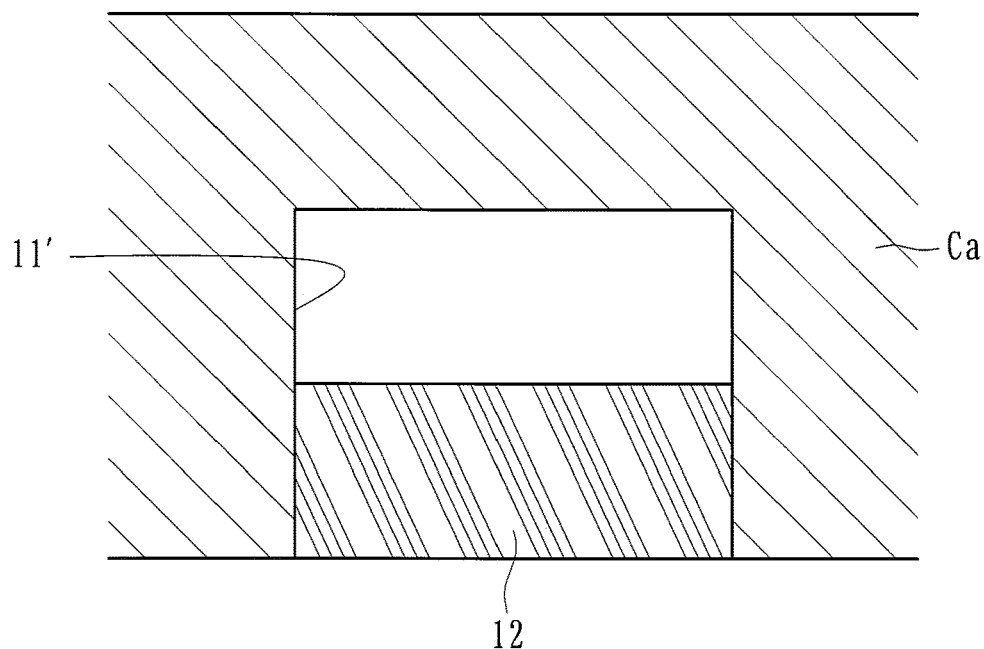
[Fig. 25]
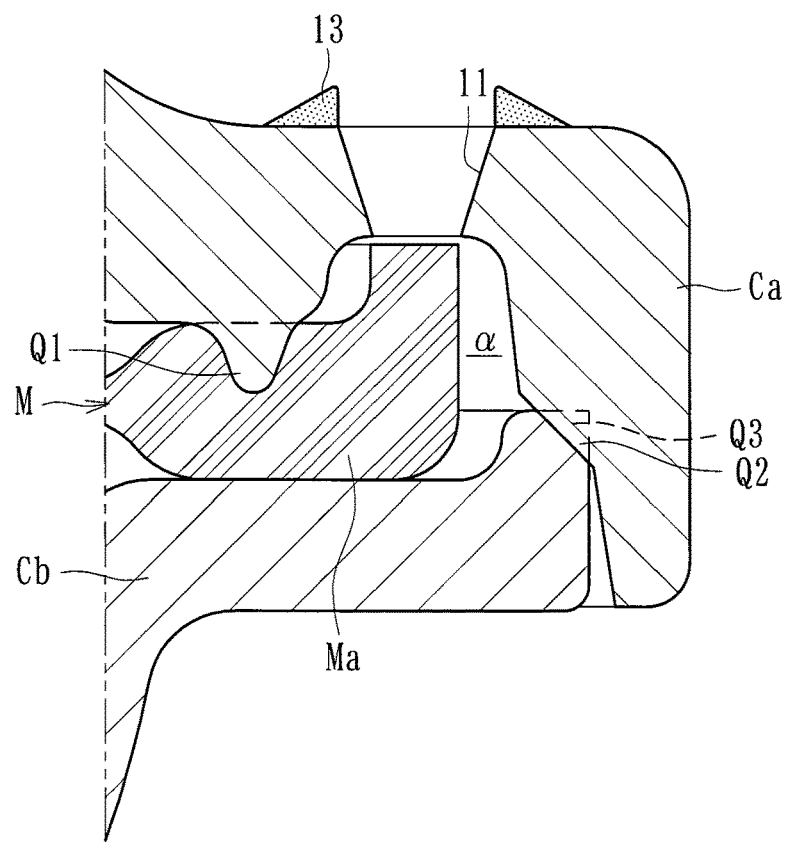

[ Fig. 26 ]
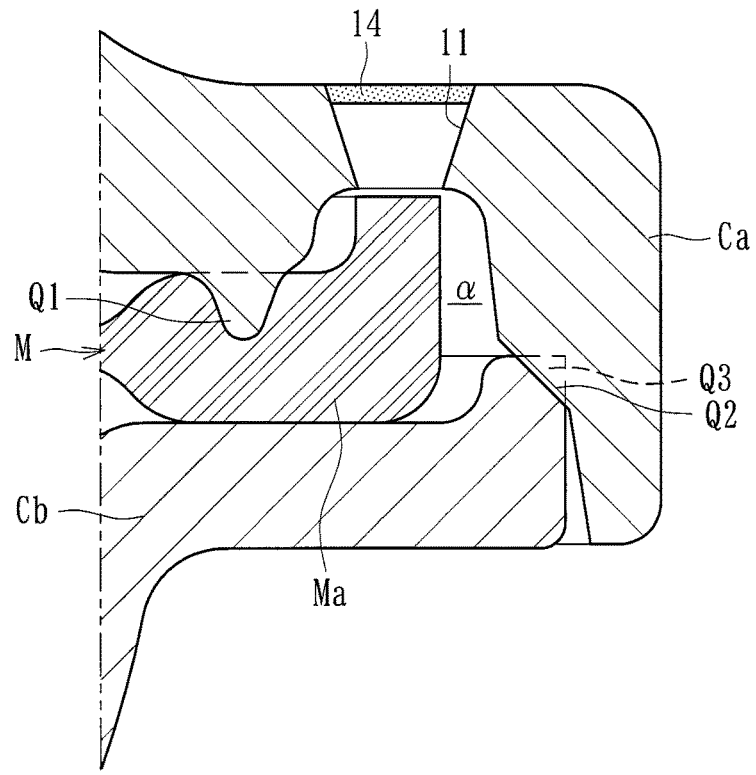
[ Fig. 27 ]
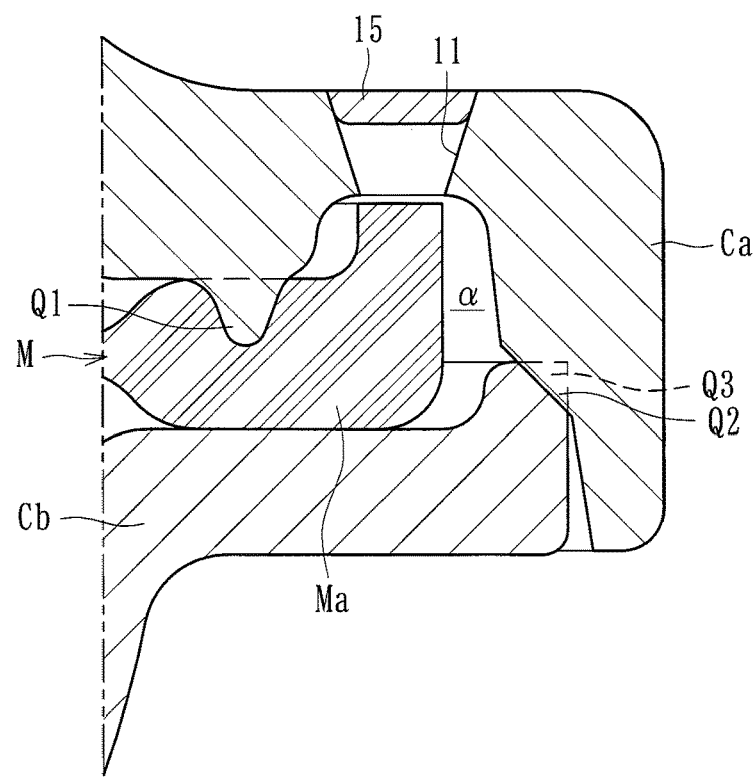

[Fig. 28]
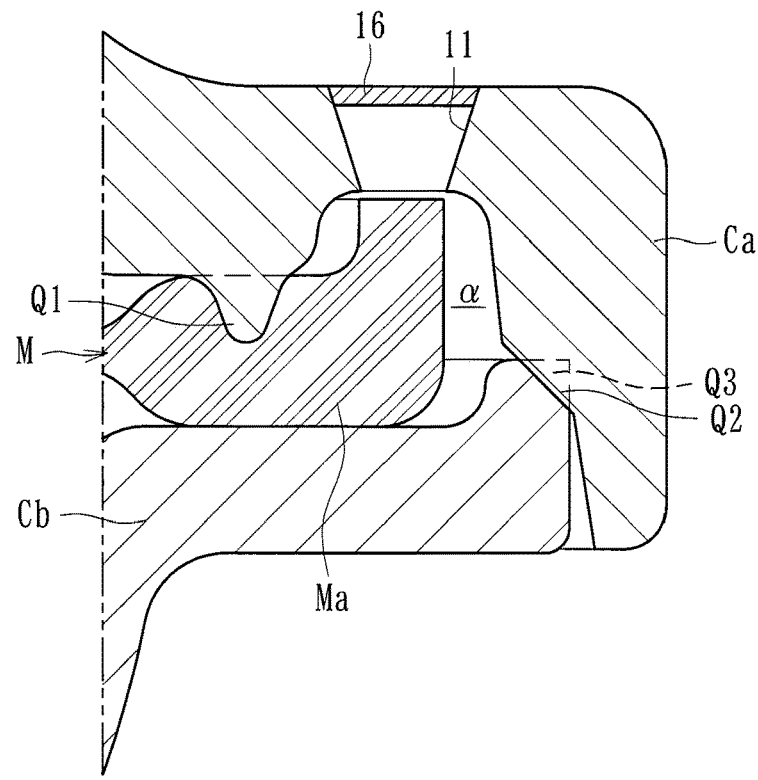
[Fig. 29]
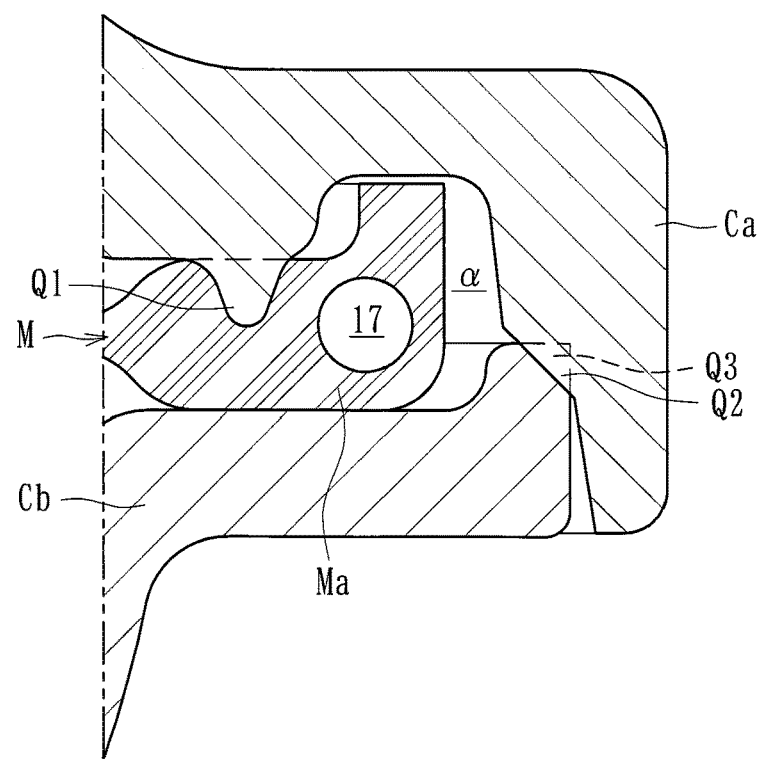

[Fig. 30]
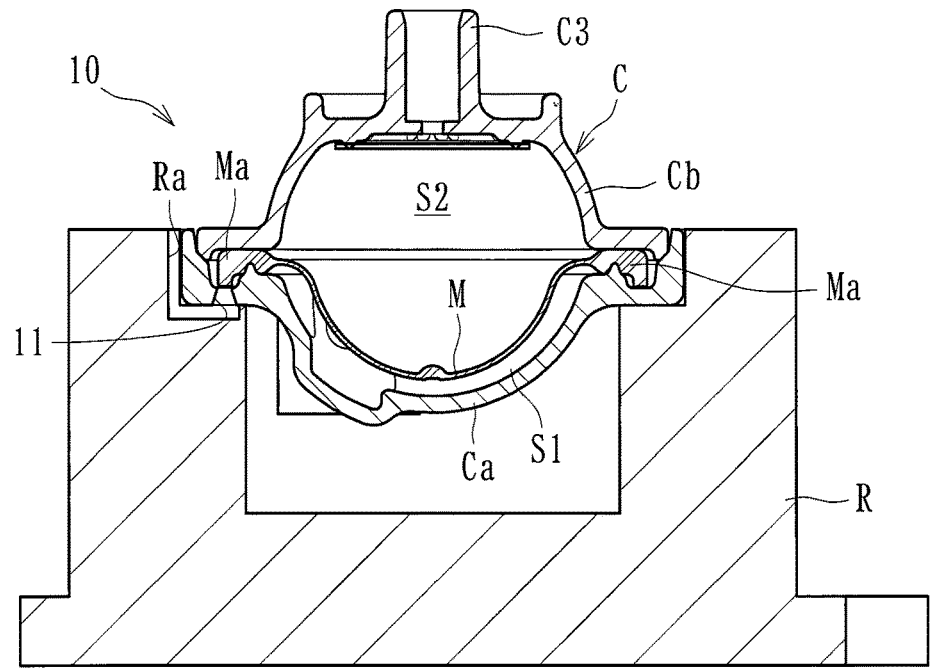
[Fig. 31]
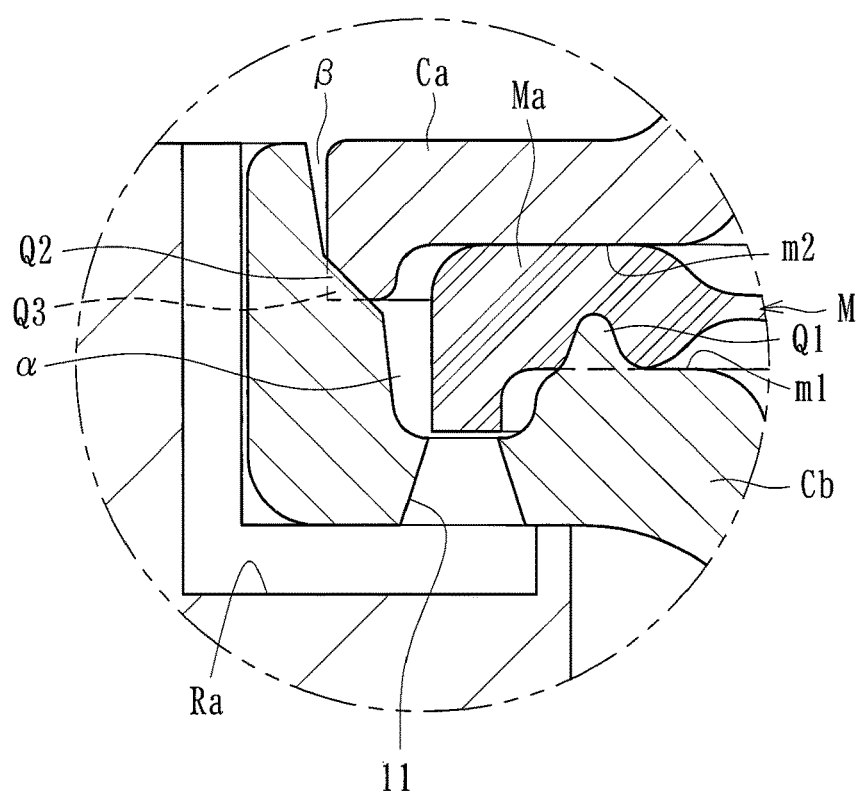

[Fig. 32]
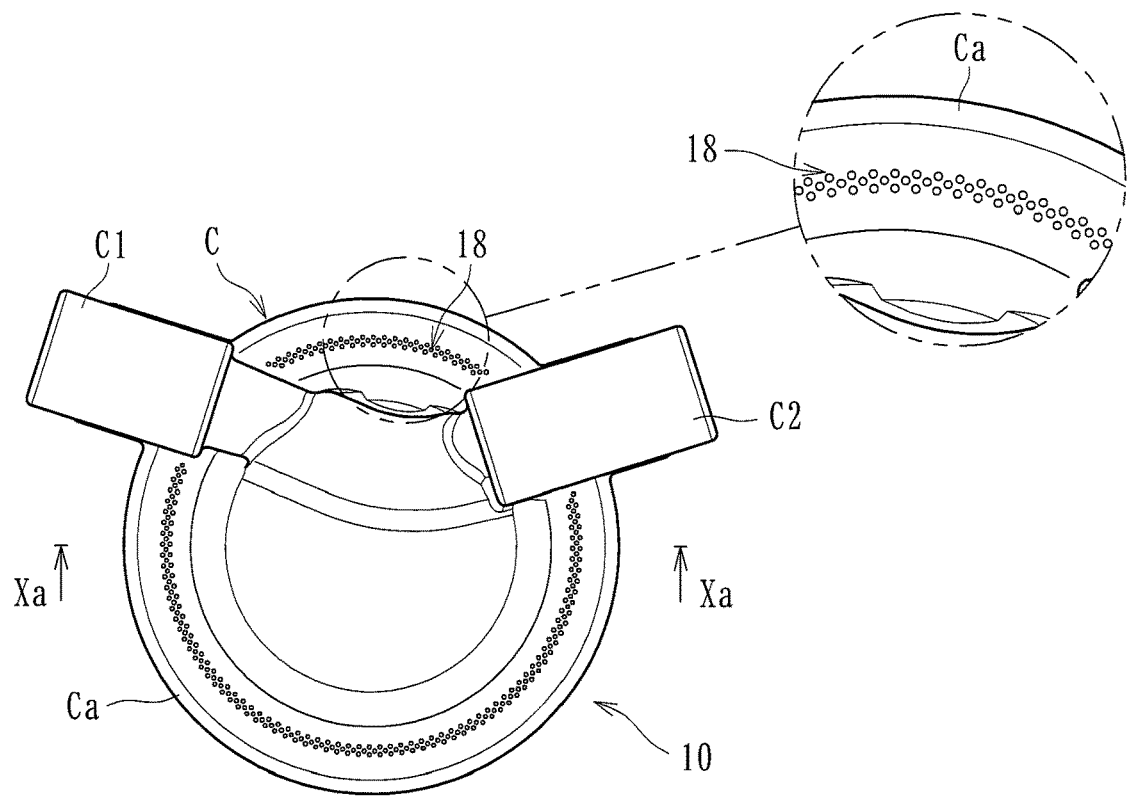
[Fig. 33]
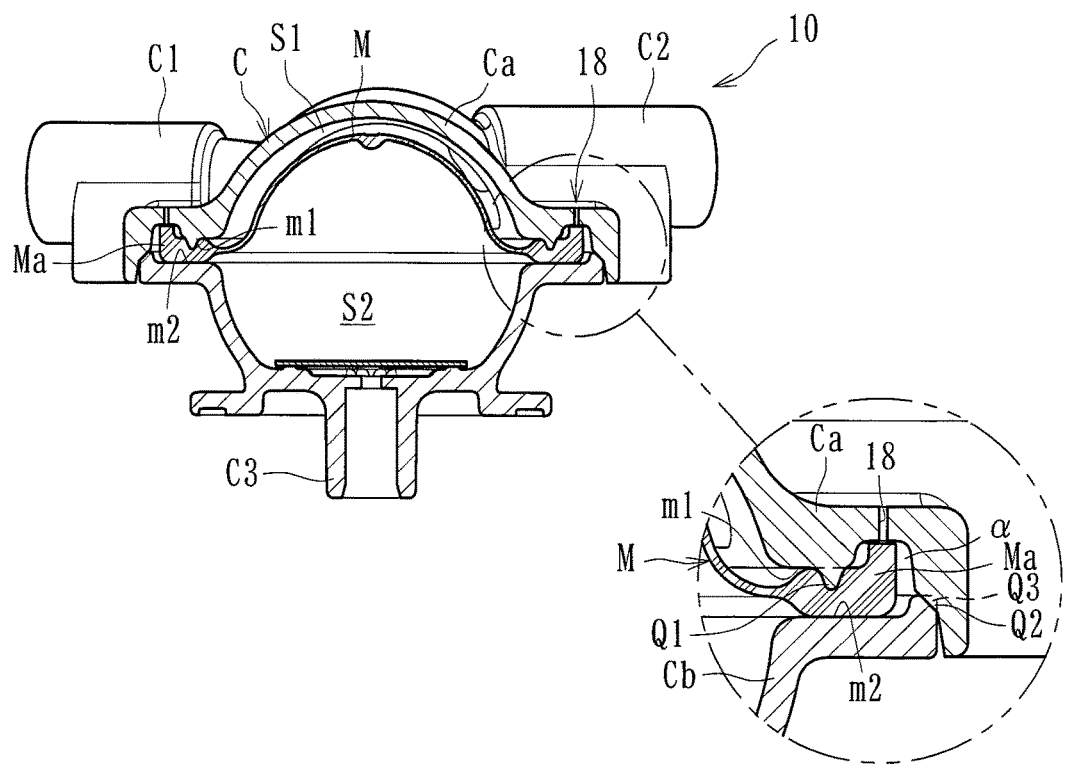

[ Fig. 34 ]
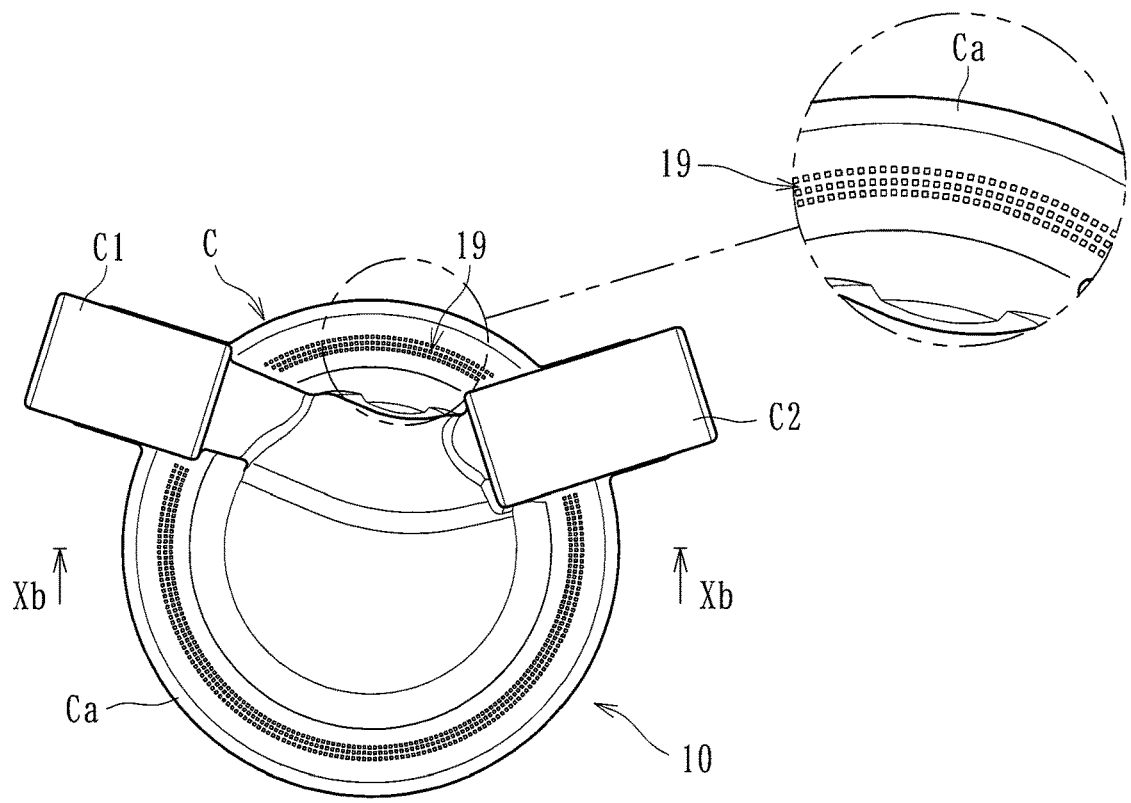
[ Fig. 35 ]
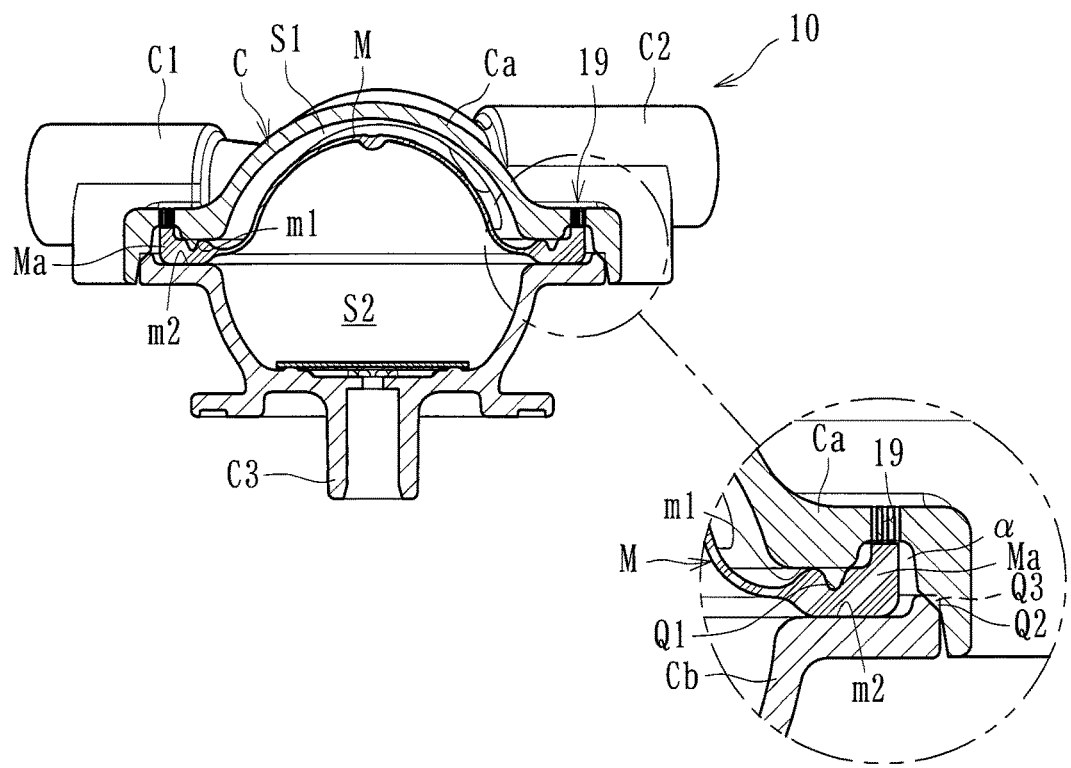

[Fig. 36]
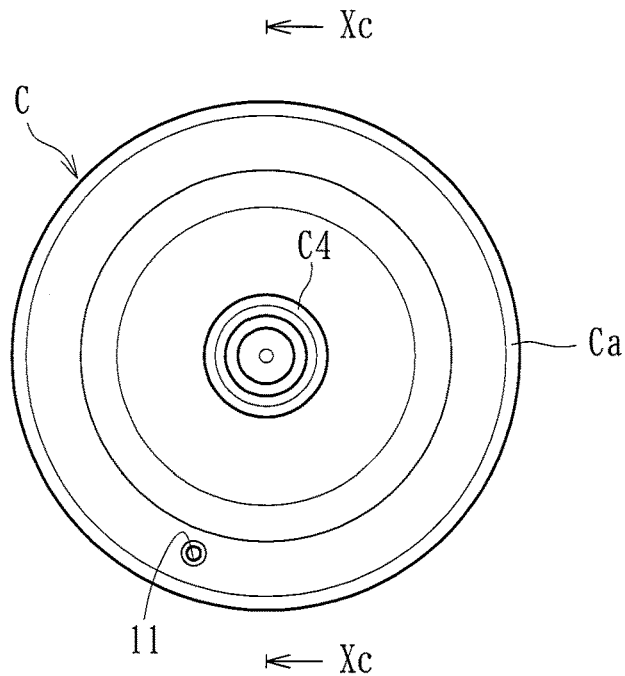
[Fig. 37]
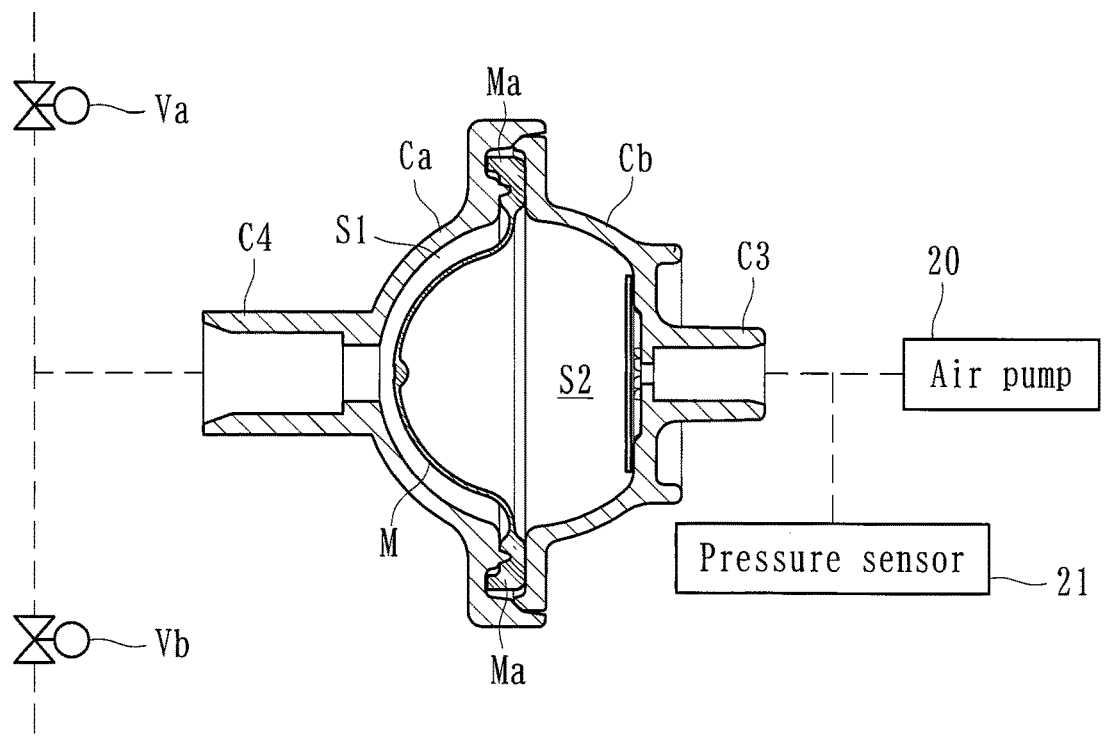

[ Fig. 38 ]
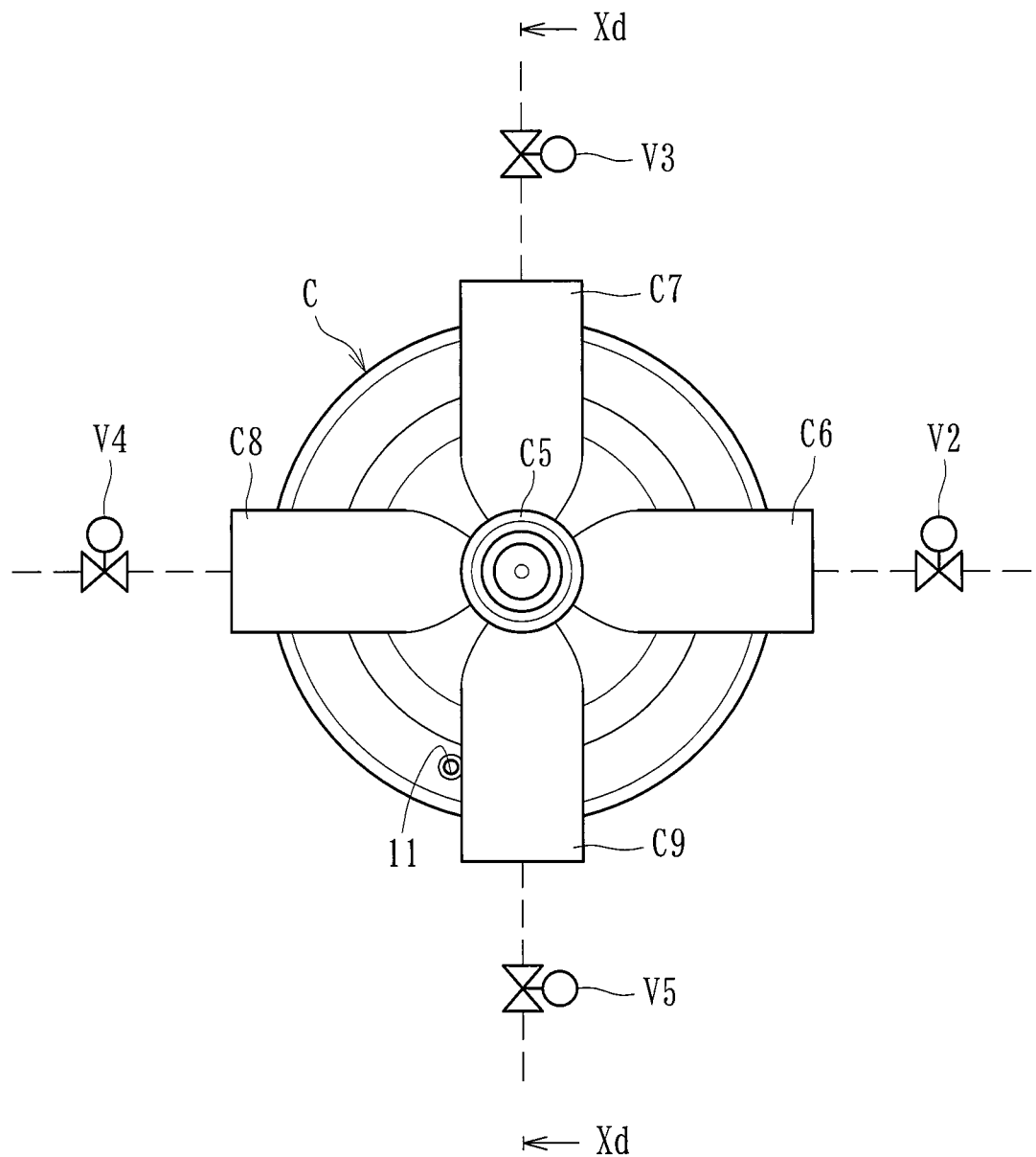

[Fig. 39]
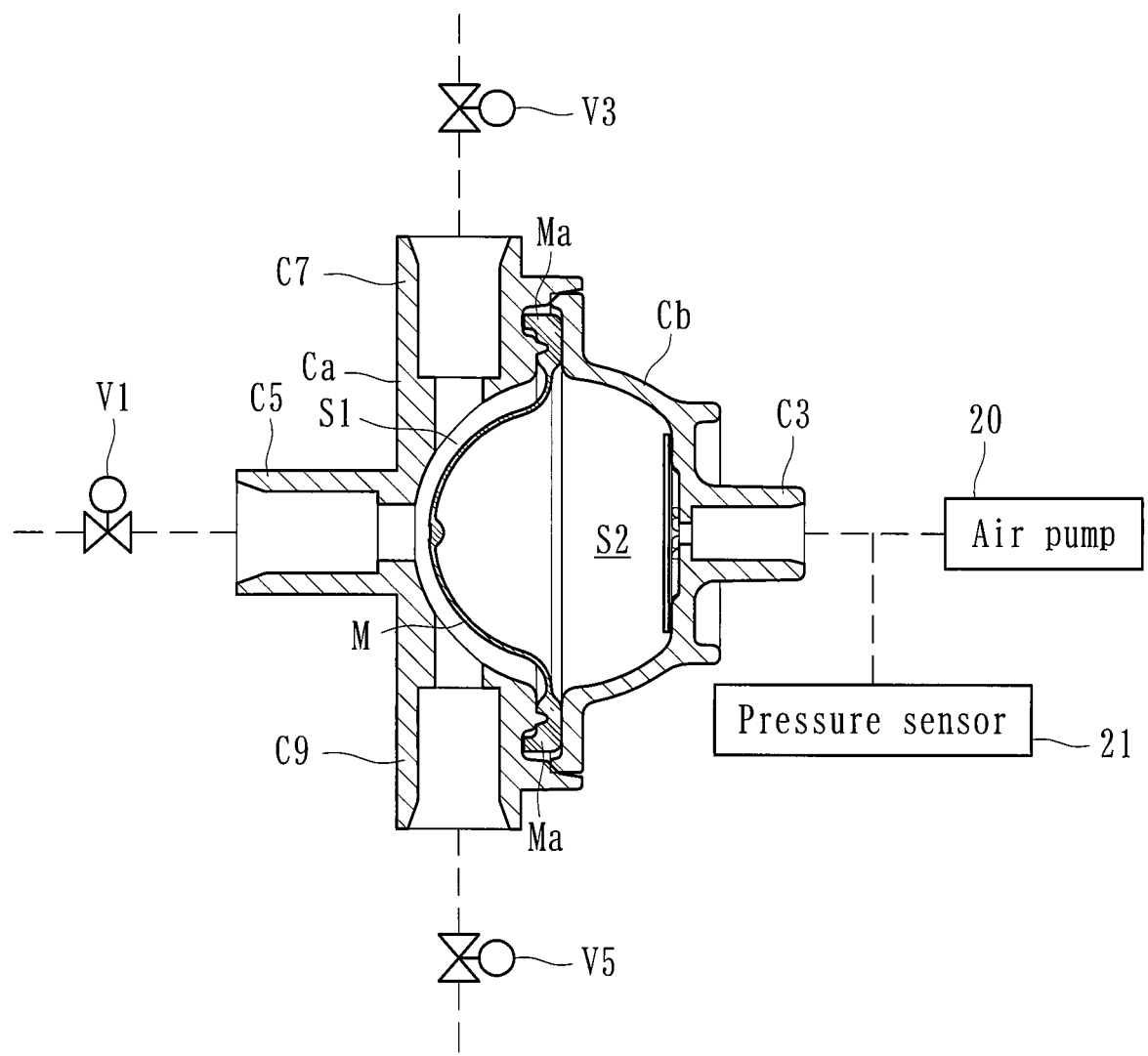

MEDICAL DEVICE AND METHOD OF MANUFACTURING THE SAME

CROSS-REFERENCE TO RELATED APPLICATION(S)

This application is a continuation of International Application No. PCT/JP2019/024655, filed on Jun. 21, 2019, which claims priority to Japanese Application No. 2018-119262, filed on Jun. 22, 2018, the entire disclosures of which are hereby incorporated by reference.

FIELD

The present application relates to a medical device including an elastic membrane with which a first housing space covered by a first case portion and a second housing space covered by a second case portion are separated from each other, and also relates to a method of manufacturing the same.

BACKGROUND

In general, dialysis treatment is performed by using a blood circuit for causing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and a venous puncture needle, respectively. The patient is punctured with the puncture needles, and extracorporeal circulation of blood in the dialysis treatment is thus performed.

To detect the pressure of blood that extracorporeally circulates through a blood circuit, a pressure detector has been proposed as disclosed by PTL 1, for example. The pressure detector includes a case connectable to a blood circuit, and a diaphragm (a membrane member) attached inside the case and with which a liquid-phase portion to be supplied with blood in the blood circuit and a gas-phase portion to be supplied with air are separated from each other, the diaphragm being displaceable in accordance with the pressure of the blood supplied to the liquid-phase portion, the pressure detector being capable of detecting the pressure of the blood by detecting the pressure in the gas-phase portion with a pressure detection sensor. With such a known pressure detector, since the liquid-phase portion and the gas-phase portion are separated from each other by the membrane member, the pressure of the blood in the blood circuit can be detected accurately while the blood is prevented from touching the air in the gas-phase portion.

PTL 1: JP2017-504389 (a Published Japanese Translation of a PCT Application) the teachings of which are expressly incorporated by reference herein for all purposes.

SUMMARY

In the above known pressure detector, when the half-piece cases (the first case portion and the second case portion) are mated to each other and the peripheries thereof are fixed to each other by ultrasonic welding or the like, the entirety of the peripheral edge of the diaphragm is sealed by a sealing part provided on the first case portion or the second case portion. Therefore, a closed space is produced between the sealing part and the fixing part (the welded part). Consequently, in the welding process, the pressure in the closed space may increase excessively.

If the pressure in the closed space increase excessively in a case where the pressure detector as a finished product is subjected to, for example, autoclave sterilization, annealing, or a high-temperature environment of use, the pressure in the closed space further increases to possibly displace the diaphragm in the radial direction and reduce the sealability, resulting in a defective or malfunctioning product. In particular, if press-fitting such as ultrasonic welding is performed in fixing the first case portion and the second case portion to each other, the pressure increase in the closed space is significant, which increases the probability of radial displacement of the diaphragm.

Such a problem is not specific to pressure detectors including diaphragms and also occurs in other medical devices each including an elastic membrane with which housing spaces in a first case portion and a second case portion are separated from each other. The present applicant has decided to thoroughly examine the way of improvements in quality and reliability of such a medical device by suppressing the occurrence of excessive pressure increase in an air gap produced between the sealing part and the fixing part.

The present invention has been conceived in view of the above circumstances and provides a medical device and a method of manufacturing the same in which the occurrence of excessive pressure increase in an air gap produced between a sealing part and a fixing part is suppressed for improvements in quality and reliability.

Variation 1 may comprise a medical device including a case obtained by mating a first case portion and a second case portion to each other, the case having a housing space inside; an elastic membrane as an elastic member attached to the case and with which a first housing space covered by the first case portion and a second housing space covered by the second case portion are separated from each other; fixing parts provided at respective peripheries of the first case portion and the second case portion and at which the first case portion and the second case portion that are mated to each other are fixed to each other; holding surfaces provided at the respective peripheries of the first case portion and the second case portion and between which a peripheral edge of the elastic membrane is held; and a sealing part provided at the periphery of the first case portion or the second case portion on an inner side with respect to the fixing parts and that seals an entirety of the peripheral edge of the elastic membrane held between the holding surfaces. The medical device has a releasing part that releases a pressure in an air gap produced between the sealing part and the fixing parts.

Variation 2 may comprise the medical device according to variation 1, when the first case portion and the second case portion are fixed to each other at the fixing parts, the releasing part releases the pressure generated in the air gap.

Variation 3 may comprise the medical device according to variations 1 or 2, the case is connectable to a flow route for liquid; the first housing space serves as a liquid-phase portion to be supplied with the liquid in the flow route; the second housing space serves as a gas-phase portion to be supplied with gas; the elastic membrane is a membrane member with which the liquid-phase portion and the gas-phase portion are separated from each other and that is displaceable in accordance with a pressure of the liquid supplied into the liquid-phase portion; and the medical device serves as a pressure detector that detects the pressure of the liquid in the flow route by detecting a pressure in the gas-phase portion.

Variation 4 may comprise the medical device according to variations 1 to 3, the releasing part serves as a connecting part that connects the air gap and an outside of the case to each other.

Variation 5 may comprise the medical device according to variation 4, when the first case portion and the second case portion are fixed to each other at the fixing parts, the connecting part releases the pressure generated in the air gap and is closed by melting of a projected part provided at an edge of an opening of the connecting part or with a separately prepared plug member or filter member.

Variation 6 may comprise the medical device according to variations 1 to 3, the releasing part serves as a connecting groove provided in the holding surface of the first case portion or the second case portion and that connects the air gap and the first housing space or the second housing space to each other; and when the first case portion and the second case portion are fixed to each other at the fixing parts, the releasing part releases the pressure generated in the air gap and is closed by the elastic membrane.

Variation 7 may comprise the medical device according to variations 1 to 3, the releasing part serves as a cut part provided in a region of the fixing part of the first case portion or the second case portion.

Variation 8 may comprise the medical device according to variation 7, when the first case portion and the second case portion are fixed to each other at the fixing parts, the cut part releases the pressure generated in the air gap and is closed with melting or deformation of the fixing parts or regions around the fixing parts.

Variation 9 may comprise the medical device according to variations 1 to 3, when the first case portion and the second case portion are fixed to each other at the fixing parts, the releasing part releases the pressure in the air gap by being bent outward or displaced under the pressure generated in the air gap.

Variation 10 may comprise a method of manufacturing a medical device, the medical device including a case obtained by mating a first case portion and a second case portion to each other, the case having a housing space inside; an elastic membrane as an elastic member attached to the case and with which a first housing space covered by the first case portion and a second housing space covered by the second case portion are separated from each other; fixing parts provided at respective peripheries of the first case portion and the second case portion and at which the first case portion and the second case portion that are mated to each other are fixed to each other; holding surfaces provided at the respective peripheries of the first case portion and the second case portion and between which a peripheral edge of the elastic membrane is held; and a sealing part provided at the periphery of the first case portion or the second case portion on an inner side with respect to the fixing parts and that seals an entirety of the peripheral edge of the elastic membrane held between the holding surfaces. The method includes releasing a pressure in an air gap produced between the sealing part and the fixing parts.

Variation 11 may comprise the method of manufacturing a medical device according to variation 10, when the first case portion and the second case portion are fixed to each other at the fixing parts, the pressure generated in the air gap is released.

Variation 12 may comprise the method of manufacturing a medical device according to variations 10 or 11, the case is connectable to a flow route for liquid; the first housing space serves as a liquid-phase portion to be supplied with the liquid in the flow route; the second housing space serves as a gas-phase portion to be supplied with gas; the elastic membrane is a membrane member with which the liquid-phase portion and the gas-phase portion are separated from each other and that is displaceable in accordance with a pressure of the liquid supplied into the liquid-phase portion; and the medical device serves as a pressure detector that detects the pressure of the liquid in the flow route by detecting a pressure in the gas-phase portion.

Variation 13 may comprise the method of manufacturing a medical device according to variations 10 to 12, the pressure in the air gap is released through a connecting part that connects the air gap and an outside of the case to each other.

Variation 14 may comprise the method of manufacturing a medical device according to variation 13, when the first case portion and the second case portion are fixed to each other at the fixing parts, the pressure generated in the air gap is released through the connecting part and the connecting part is closed by melting of a projected part provided at an edge of an opening of the connecting part or with a separately prepared plug member or filter member.

Variation 15 may comprise the method of manufacturing a medical device according to variations 10 to 12, when the first case portion and the second case portion are fixed to each other at the fixing parts, the pressure generated in the air gap is released through a connecting groove provided in the holding surface of the first case portion or the second case portion and that connects the air gap and the first housing space or the second housing space to each other and the connecting groove is closed by the elastic membrane.

Variation 16 may comprise the method of manufacturing a medical device according to variations 10 to 12, the pressure in the air gap is released through a cut part provided in a region of the fixing part of the first case portion or the second case portion.

Variation 17 may comprise the method of manufacturing a medical device according to variation 16, when the first case portion and the second case portion are fixed to each other at the fixing parts, the cut part releases the pressure generated in the air gap and is closed with melting or deformation of the fixing parts or regions around the fixing parts.

Variation 18 may comprise the method of manufacturing a medical device according to variations 10 to 12, when the first case portion and the second case portion are fixed to each other at the fixing parts, the pressure generated in the air gap is released by bending outward or displacing the releasing part under the pressure generated in the air gap.

Variation 19 may comprise the method of manufacturing a medical device according to variations 10 to 18, the first case portion and the second case portion that are mated to each other are fixedly set on a jig; an entirety of the peripheral edge of the elastic membrane that is held between the holding surfaces is sealed; and the jig has a jig releasing part that releases the pressure in the air gap produced between the sealing part and the fixing parts.

According to the teachings of each of variations 1 and 10, the pressure in the air gap produced between the sealing part and the fixing parts is released. Therefore, the occurrence of excessive pressure increase in the air gap produced between the sealing part and the fixing parts can be suppressed. Consequently, improvements in quality and reliability can be achieved.

According to the teachings of each of variations 2 and 11, when the first case portion and the second case portion are fixed to each other at the fixing parts, the pressure generated in the air gap is released. Therefore, if the finished medical device is subjected to autoclave sterilization, annealing, or a high-temperature environment of use, the occurrence of pressure increase in the air gap can be suppressed.

According to the teachings of each of variations 3 and 12, the case is connectable to the flow route for liquid; the first housing space serves as the liquid-phase portion to be supplied with the liquid in the flow route; the second housing space serves as the gas-phase portion to be supplied with gas; the elastic membrane is the membrane member with which the liquid-phase portion and the gas-phase portion are separated from each other and that is displaceable in accordance with the pressure of the liquid supplied into the liquid-phase portion; and the medical device serves as a pressure detector that detects the pressure of the liquid in the flow route by detecting the pressure in the gas-phase portion. Therefore, the occurrence of excessive pressure increase in the air gap produced between the sealing part and the fixing parts is suppressed. Consequently, the quality and reliability of the pressure detector can be improved.

According to the teachings of each of variations 4 and 13, the pressure in the air gap is released through the connecting part connecting the air gap and the outside of the case to each other. Therefore, the occurrence of excessive pressure increase in the air gap can be suppressed more assuredly and smoothly.

According to the teachings of each of variations 5 and 14, when the first case portion and the second case portion are fixed to each other at the fixing parts, the connecting part releases the pressure generated in the air gap and is closed by melting of the projected part provided at the edge of the opening of the connecting part or with the separately prepared plug member or filter member. Therefore, the connecting part of the finished medical device can be prevented from being left open. Consequently, entry of foreign substances or the like into the opening of the connecting part can be prevented.

According to the teachings of each of variations 6 and 15, when the first case portion and the second case portion are fixed to each other at the fixing parts, the connecting groove provided in the holding surface of the first case portion or the second case portion and connecting the air gap and the first housing space or the second housing space to each other not only releases the pressure generated in the air gap but is also closed by the elastic membrane. Therefore, the occurrence of excessive pressure increase in the air gap produced between the sealing part and the fixing parts can be suppressed. Furthermore, after the pressure in the air gap is released, the connecting groove can be closed naturally.

According to the teachings of each of variations 7 and 16, the pressure in the air gap is released through the cut part provided in a region of the fixing part of the first case portion or the second case portion. That is, the pressure in the air gap can be released from the position where the fixing part is provided.

According to the teachings of each of variations 8 and 17, when the first case portion and the second case portion are fixed to each other at the fixing parts, the cut part not only releases the pressure generated in the air gap but is also closed with the melting or deformation of the fixing parts or regions therearound. Therefore, the occurrence of excessive pressure increase in the air gap produced between the sealing part and the fixing parts can be suppressed. Furthermore, after the pressure in the air gap is released, the cut part can be closed naturally.

According to the teachings of each of variations 9 and 18, when the first case portion and the second case portion are fixed to each other at the fixing parts, the releasing part releases the pressure in the air gap by being bent outward or displaced under the pressure generated in the air gap. Since the releasing part is bent outward or displaced with the pressure change, the occurrence of excessive pressure increase in the air gap produced between the sealing part and the fixing parts can be suppressed.

According to the teachings of each of variation 19, the first case portion and the second case portion that are mated to each other are fixedly set on the jig; the entirety of the peripheral edge of the elastic membrane that is held between the holding surfaces is sealed; and the jig has the jig releasing part that releases the pressure in the air gap produced between the sealing part and the fixing parts. Therefore, in the manufacturing process, the pressure in the air gap can be released more assuredly. Furthermore, the occurrence of relative displacement between the first case portion and the second case portion can be suppressed. Consequently, the first case portion and the second case portion can be fixed to each other accurately.

BRIEF DESCRIPTION OF THE DRAWINGS

FIG. 1 is a schematic diagram of a dialysis apparatus (a blood purification apparatus) to which a pressure detector as a medical device according to a first embodiment of the present invention is applied.

FIG. 2 is a plan view of the pressure detector.

FIG. 3 is a front view of the pressure detector.

FIG. 4 is a sectional view taken along line IV-IV illustrated in FIG. 2 (with a membrane member displaced toward the side of a liquid-phase portion).

FIG. 5 is a sectional view taken along line IV-IV illustrated in FIG. 2 (with the membrane member displaced toward the side of a gas-phase portion).

FIG. 6 is a sectional view taken along line VI-VI illustrated in FIG. 2.

FIG. 7 is a third-angle projection of a first case portion included in the pressure detector.

FIG. 8 is a third-angle projection of a second case portion included in the pressure detector.

FIG. 9 includes a plan view and a front view of the membrane member included in the pressure detector.

FIG. 10 is an enlarged sectional view of the pressure detector and illustrates a function of releasing the pressure in an air gap through a releasing part (a connecting part).

FIG. 11 is an enlarged sectional view of the pressure detector and illustrates the function of releasing the pressure in the air gap through the releasing part (the connecting part).

FIG. 12 is an enlarged sectional view illustrating a case where the releasing part (the connecting part) is provided at another position (below the air gap).

FIG. 13 is an enlarged sectional view illustrating a case where the releasing part (the connecting part) is provided at yet another position (on a lateral side of the air gap).

FIG. 14 is an enlarged sectional view of a pressure detector according to a second embodiment of the present invention and illustrates a releasing part (a connecting groove).

FIG. 15 is a sectional view taken along line XV-XV illustrated in FIG. 14.

FIG. 16 is a plan view of a second case portion having the releasing part (the connecting groove).

FIG. 17 is an enlarged sectional view illustrating a state where the releasing part (the connecting groove) is closed.

FIG. 18 is a sectional view taken along line XVIII-XVIII illustrated in FIG. 17.

FIG. 19 is an enlarged sectional view of a pressure detector according to a third embodiment of the present invention and illustrates a releasing part (a cut part).

FIG. 20 is a plan view of a second case portion having the releasing part (the cut part).

FIG. 21 is an enlarged sectional view illustrating a state established before a fixing part of the second case portion having the releasing part (the cut part) and a fixing part of a first case portion are fixed to each other.

FIG. 22 is an enlarged sectional view illustrating a state established after the fixing part of the second case portion having the releasing part (the cut part) and the fixing part of the first case portion are fixed to each other.

FIG. 23 is an enlarged sectional view of a pressure detector according to another embodiment of the present invention and illustrates a releasing part (a flexible component provided in a connecting part).

FIG. 24 is an enlarged sectional view of a pressure detector according to yet another embodiment of the present invention and illustrates a releasing part (a flexible component provided in a recess).

FIG. 25 is an enlarged sectional view of a pressure detector according to yet another embodiment of the present invention and illustrates a state established before a releasing part (a connecting part) is closed.

FIG. 26 is an enlarged sectional view illustrating a state established after the releasing part (the connecting part) is closed.

FIG. 27 is an enlarged sectional view of a pressure detector according to yet another embodiment of the present invention and illustrates a releasing part (a plug member provided in a connecting part).

FIG. 28 is an enlarged sectional view of a pressure detector according to yet another embodiment of the present invention and illustrates a releasing part (a filter member provided in a connecting part).

FIG. 29 is an enlarged sectional view of a pressure detector according to yet another embodiment of the present invention and illustrates a releasing part (a closed space provided in a membrane member M).

FIG. 30 is a schematic sectional view of a jig for manufacturing a pressure detector according to the present invention.

FIG. 31 is an enlarged view of the jig.

FIG. 32 is a plan view of a pressure detector according to yet another embodiment of the present invention (with a plurality of connecting parts (each having a circular opening) aligned in the circumferential direction thereof).

FIG. 33 is a sectional view taken along line Xa-Xa illustrated in FIG. 32.

FIG. 34 is a plan view of a pressure detector according to yet another embodiment of the present invention (with a plurality of connecting parts (each having a rectangular opening) aligned in the circumferential direction thereof).

FIG. 35 is a sectional view taken along line Xb-Xb illustrated in FIG. 34.

FIG. 36 is a plan view of a diaphragm pump (a pump including a gas-phase-portion case with a single port) as a medical device according to yet another embodiment of the present invention.

FIG. 37 is a sectional view taken along line Xc-Xc illustrated in FIG. 36.

FIG. 38 is a plan view of a diaphragm pump (a pump including a gas-phase-portion case with five ports) as a medical device according to yet another embodiment of the present invention.

FIG. 39 is a sectional view taken along line Xd-Xd illustrated in FIG. 38.

DETAILED DESCRIPTION

Embodiments of the present invention will now be described specifically with reference to the drawings.

A blood purification apparatus applied to a first embodiment is a dialysis apparatus for giving dialysis treatment and basically includes, as illustrated in FIG. 1, a blood circuit including an arterial blood circuit 1 and a venous blood circuit 2, a dialyzer 3 (a blood purifier) provided between the arterial blood circuit 1 and the venous blood circuit 2 and that purifies blood flowing through the blood circuit, a blood pump 4, an air-trap chamber 5 provided to the venous blood circuit 2, a dialysis device 6 that supplies dialysate to the dialyzer 3 and drains waste liquid from the dialyzer 3, a physiological-saline supply line L3 (a substitution-fluid supply line) that allows physiological saline as a substitution fluid to be supplied to the blood circuit, and a storage unit 7 that stores the physiological saline as the substitution fluid.

The arterial blood circuit 1 is provided with an arterial puncture needle (a) connectable to a distal end thereof through a connector, and the blood pump 4, which is of a peristaltic type, at a halfway position thereof. The venous blood circuit 2 is provided with a venous puncture needle (b) connectable to a distal end thereof through a connector, and the air-trap chamber 5 at a halfway position thereof. The air-trap chamber 5 is capable of trapping bubbles in the liquid and is provided with a filtering net (not illustrated), thereby being capable of trapping, for example, thrombi and the like at the time of blood return. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The blood pump 4, which is a peristaltic pump provided to the arterial blood circuit 1, is capable of undergoing normal rotation and reverse rotation and causing the liquid in the blood circuit to flow in the direction of rotation thereof. Specifically, the arterial blood circuit 1 includes a squeezable tube that is softer and has a larger diameter than other flexible tubes forming the arterial blood circuit 1. The blood pump 4 includes rollers for squeezing the squeezable tube in the direction of liquid delivery. When the blood pump 4 is activated, the rollers rotate and thus squeeze the squeezable tube (a portion of the blood circuit), whereby the liquid in the tube can be made to flow in the direction of rotation (the direction in which the rollers rotate).

When the blood pump 4 is activated to undergo normal rotation (leftward rotation in the drawing) while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patients body. That is, the patient's blood is purified with the dialyzer 3 while being caused to extracorporeally circulate through the blood circuit from the distal end of the arterial blood circuit 1 to the distal end of the venous blood circuit 2. When the blood pump 4 is activated to undergo reverse rotation (rightward rotation in the drawing), the blood in the blood circuit (a portion of the arterial blood circuit 1 that is between the distal end and a position where the blood pump 4 is provided) can be returned to the patient.

The dialyzer 3 has, in a housing thereof, a blood introduction port 3a, a blood delivery port 3b, a dialysate introduction port 3c, and a dialysate delivery port 3d. The blood introduction port 3a is connected to the arterial blood circuit 1. The blood delivery port 3b is connected to the venous blood circuit 2. The dialysate introduction port 3c and the dialysate delivery port 3d are connected to a dialysate introduction line L1 and a dialysate drain line L2, respectively, extending from the dialysis device 6.

The dialyzer 3 houses a plurality of hollow fibers. Spaces inside the respective hollow fibers form flow routes for blood, and spaces between the inner surface of the housing and the outer surfaces of the hollow fibers form flow routes for dialysate. The hollow fibers each have a number of microscopic holes (pores) extending therethrough from the outer surface to the inner surface, thereby forming a hollow fiber membrane. Impurities and the like contained in the blood are allowed to permeate through the hollow fiber membranes into the dialysate.

On the other hand, the dialysis device 6 includes a liquid delivery unit such as a duplex pump provided over the dialysate introduction line L1 and the dialysate drain line L2. A bypass line that bypasses the liquid delivery unit is provided with an ultrafiltration pump for removing water from the patient's blood flowing in the dialyzer 3. One end of the dialysate introduction line L1 is connected to the dialyzer 3 (the dialysate introduction port 3c), and the other end is connected to a dialysate supply device (not illustrated) that prepares a dialysate at a predetermined concentration. One end of the dialysate drain line L2 is connected to the dialyzer 3 (the dialysate delivery port 3d), and the other end is connected to a drainage unit, not illustrated. The dialysate supplied from the dialysate supply device flows through the dialysate introduction line L1 into the dialyzer 3, and further flows through the dialysate drain line L2 into the drainage unit.

The air-trap chamber 5 is provided with an overflow line extending from the top thereof. The overflow line is provided with a clamp unit, such as an electromagnetic valve, at a halfway position thereof. When the clamp unit such as an electromagnetic valve is opened, the liquid (a priming solution or the like) flowing in the blood circuit can be made to overflow through the overflow line.

The physiological-saline supply line L3 (the substitution-fluid supply line) is connected at one end thereof to the arterial blood circuit 1 between the position where the blood pump 4 is provided and the distal end of the arterial blood circuit 1 through a T-shaped pipe or the like. The physiological-saline supply line L3 forms a flow route (such as a flexible tube or the like) through which the physiological saline (the substitution fluid) to substitute for the blood in the blood circuit is allowed to be supplied to the arterial blood circuit 1. The physiological-saline supply line L3 is provided at the other end thereof with the storage unit 7 (a so-called "saline bag"), in which a predetermined amount of physiological saline is stored. The physiological-saline supply line L3 is further provided at a halfway position thereof with an air-trap chamber 8.

The physiological-saline supply line L3 according to the present embodiment is further provided with a clamp unit 9 (such as an electromagnetic valve or the like). The clamp unit 9 is capable of opening and closing the physiological-saline supply line L3, thereby closing and opening the flow route. The state of the physiological-saline supply line L3 is arbitrarily switchable by opening or closing the clamp unit 9, between a closed state where the flow route is closed and an open state where the physiological saline (the substitution fluid) is allowed to flow. The clamp unit 9 may be replaced with a general-purpose device such as a pair of forceps with which the flow route of the physiological-saline supply line L3 can be manually closed and opened.

The blood circuit applied to the present embodiment is provided with a pressure detector 10 as a medical device. The pressure detector 10 is connected to the venous blood circuit 2 at a position between the dialyzer 3 and the air-trap chamber 5 and is capable of detecting the pressure of the blood flowing in the venous blood circuit 2 (the blood circuit). Specifically, as illustrated in FIGS. 2 to 6, the pressure detector 10 includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P.

The case C is a hollow molded component obtained by molding a predetermined resin material or the like. The case C is a combination of a liquid-phase-portion case Ca defining the liquid-phase portion S1 and a gas-phase-portion case Cb defining the gas-phase portion S2. Specifically, the case C is obtained by mating the liquid-phase-portion case Ca (a first case portion) and the gas-phase-portion case Cb (a second case portion) to each other and having a housing space inside. The liquid-phase-portion case Ca has an inlet port C1 and an outlet port C2 integrally molded therewith. The inlet port C1 and the outlet port C2 are each connectable to the flow route for liquid and allow the flow route to communicate with the liquid-phase portion S1. The gas-phase-portion case Cb has a connection port C3 integrally molded therewith. The connection port C3 is connectable to one end of a pipe portion K, to be described below, and allows the one end to communicate with the gas-phase portion S2. The functions of the inlet port C1 and the outlet port C2 of introducing and discharging the liquid may be switched therebetween (that is, the liquid may be discharged from the inlet port C1 while being introduced into the outlet port C2).

The liquid-phase-portion case Ca has an annular holding surface m1 (see FIG. 7) at the outer periphery thereof. The gas-phase-portion case Cb has an annular holding surface m2 (see FIG. 8) at the outer periphery thereof. When the liquid-phase-portion case Ca and the gas-phase-portion case Cb are mated to each other, a periphery Ma of the membrane member M is placed between the holding surface m1 and the holding surface m2. Thus, the membrane member M can be attached in a sealed manner. A space thus provided in the case C is separated (sectioned) by the membrane member M into the liquid-phase portion S1 and the gas-phase portion S2.

The membrane member M serves as a diaphragm provided in the case C and is made of a flexible material that is displaceable or deformable in conformity with pressure change occurring in the liquid-phase portion S1 or the gas-phase portion S2. The membrane member M according to the present embodiment is an elastic member attached to the case C and with which the liquid-phase portion S1 (a first housing space) covered by the liquid-phase-portion case Ca (the first case portion) and the gas-phase portion S2 (a second housing space) covered by the gas-phase-portion case Cb (the second case portion) are separated from each other. As illustrated in FIG. 9, the periphery Ma of the membrane member M projects laterally so as to be held between the holding surfaces m1 and m2. If the pressure of the liquid (the hydraulic pressure) in the liquid-phase portion S1 is low, as illustrated in FIG. 4, the membrane member M is displaced toward the side of the liquid-phase portion S1, whereby the capacity of the gas-phase portion S2 is increased. If the pressure of the liquid (the hydraulic pressure) in the liquid-phase portion S1 is high, as illustrated in FIG. 5, the membrane member M is displaced toward the side of the gas-phase portion S2, whereby the capacity of the gas-phase portion S2 is reduced.

The gas-phase-portion case Cb has an opening Cb1 (see FIG. 8) substantially at the center of the bottom thereof. The opening Cb1 provided in the inner surface (the bottom) of the gas-phase-portion case Cb allows the flow route in the connection port C3 and the gas-phase portion S2 to communicate with each other. Accordingly, air (gas) is allowed to be introduced into or discharged from the gas-phase portion S2 in accordance with the displacement of the membrane member M. The pipe K is connected at one end thereof to the connection port C3 and at the other end thereof to the pressure detection sensor P (a pressure-detecting unit). Therefore, as air (gas) is introduced or discharged through the opening Cb1 with the displacement of the membrane member M, the pressure detection sensor P can detect the pressure in the gas-phase portion S2. Note that the connection port C3 is not limited to the one to be connected to the pipe K and may be connected to another element capable of transmitting the pressure in the gas-phase portion case Cb to the pressure detection sensor P. Furthermore, as illustrated in FIG. 8, the gas-phase portion S2 has a plurality of ribs Cb2 in recesses Cb4 and around the opening Cb1. The ribs Cb2 project radially about the opening Cb1.

The inlet port C1 according to the present embodiment is a portion (a projected portion) connectable to the flow route for liquid (the blood circuit) and includes, as illustrated in FIGS. 4 and 5, a flow-route portion C1a through which the liquid (blood) flows into an inlet opening Ca1 (see FIG. 7) of the liquid-phase portion S1, and a connecting portion C1b connectable to the flow route (the blood circuit). Specifically, the flow-route portion C1a and the connecting portion C1b are continuous with each other in the axial direction thereof in the projected portion forming the inlet port C1. When a tube forming the flow route is connected to the connecting portion C1b, the liquid in the flow route can be made to flow into the flow-route portion C1a and then into the liquid-phase portion S1 through the inlet opening Ca1. Note that the inlet port C1 may be shaped as a recess to which the tube forming the flow route is to be connected.

The outlet port C2 according to the present embodiment is a portion (a projected portion) connectable to the flow route for liquid (the blood circuit) and includes, as illustrated in the drawings, a flow-route portion C2a through which the liquid (blood) having flowed into the liquid-phase portion S1 is discharged from an outlet opening Ca2 (see FIG. 7), and a connecting portion C2b connectable to the flow route (the blood circuit). Specifically, the flow-route portion C2a and the connecting portion C2b are continuous with each other in the axial direction thereof in the projected portion forming the outlet port C2. When a tube forming the flow route is connected to the connecting portion C2b, the liquid having flowed into the liquid-phase portion S1 can be made to flow into the flow-route portion C2a and then to be discharged to a flow route (the blood circuit) on the downstream side. Note that the outlet port C2 may be shaped as a recess to which the tube forming the flow route is to be connected.

As illustrated in FIGS. 10 and 11, the liquid-phase-portion case Ca (the first case portion) and the gas-phase-portion case Cb (the second case portion) have fixing parts Q2 and Q3 at the respective peripheries thereof. Furthermore, the liquid-phase-portion case Ca has a sealing part Q1 at the periphery thereof on the inner side with respect to the fixing parts Q2 and Q3 (on the inner side of the liquid-phase-portion case Ca and the gas-phase-portion case Cb). In the present embodiment, the sealing part Q1 is provided only at the periphery of the liquid-phase-portion case Ca. Alternatively, the sealing part Q1 may be provided only at the periphery of the gas-phase-portion case Cb on the inner side with respect to the fixing parts Q2 and Q3, or at each of the peripheries of the liquid-phase-portion case Ca and the gas-phase-portion case Cb on the inner side with respect to the fixing parts Q2 and Q3.

The fixing parts Q2 and Q3 are provided at the respective peripheries of the liquid-phase-portion case Ca and the gas-phase-portion case Cb and for fixing the liquid-phase-portion case Ca and the gas-phase-portion case Cb to each other in a state where the two are mated to each other. In the present embodiment, as illustrated in FIG. 10, when the liquid-phase-portion case Ca and the gas-phase-portion case Cb are mated to each other, the fixing parts Q2 and Q3 come into contact with each other. Furthermore, as illustrated in FIG. 11, when an ultrasonic wave is applied to the liquid-phase-portion case Ca and the gas-phase-portion case Cb that are pressed against each other, the fixing parts Q2 and Q3 melt, whereby the liquid-phase-portion case Ca and the gas-phase-portion case Cb are welded to each other. In other words, the liquid-phase-portion case Ca and the gas-phase-portion case Cb according to the present embodiment are press-bonded to each other by ultrasonic welding and are thus fixed (welded) to each other, whereby a housing space (including the liquid-phase portion S1 and the gas-phase portion S2) is provided thereinside.

The sealing part Q1 is provided at the periphery of the liquid-phase-portion case Ca or the gas-phase-portion case Cb on the inner side with respect to the fixing parts Q2 and Q3 and seals the entirety of the peripheral edge of the membrane member M held between the holding surfaces m1 and m2. In the present embodiment, as illustrated in FIG. 10, the sealing part Q1 is a ridge projecting from the holding surface m1 of the liquid-phase-portion case Ca toward the holding surface m2 of the gas-phase-portion case Cb. As illustrated in FIG. 11, in the process of melting the fixing parts Q2 and Q3 and fixing the two to each other by applying an ultrasonic wave to the liquid-phase-portion case Ca and the gas-phase-portion case Cb that are pressed against each other, the sealing part Q1 compresses the periphery Ma of the membrane member M in the thicknesswise direction and thus seals the periphery Ma.

When the liquid-phase-portion case Ca and the gas-phase-portion case Cb are fixed to each other by melting the fixing parts Q2 and Q3 and the sealing by the sealing part Q1 is thus achieved, an air gap ($\alpha$) is produced between the sealing part Q1 and the fixing parts Q2 and Q3. The air gap ($\alpha$) is a space produced in the process of bringing the liquid-phase-portion case Ca and the gas-phase-portion case Cb into contact with each other so as to be welded to each other. The air gap ($\alpha$) is sealed by the sealing part Q1. Therefore, if a releasing part 11 according to the present embodiment is not provided, the pressure thereinside may increase excessively.

The releasing part 11 is provided for releasing the pressure in the air gap (α) between the sealing part Q1 and the fixing parts Q2 and Q3 when the liquid-phase-portion case Ca (the first case portion) and the gas-phase-portion case Cb (the second case portion) are fixed to each other at the fixing parts Q2 and Q3. In the present embodiment, as illustrated in FIGS. 10 and 11, the releasing part 11 serves as a connecting part (connecting hole) that connects the air gap (α) and the outside of the case C to each other. When the liquid-phase-portion case Ca and the gas-phase-portion case Cb are welded to each other, air in the air gap (α) produced in the process of bringing the liquid-phase-portion case Ca and the gas-phase-portion case Cb into contact with each other can be released to the outside through the releasing part 11. That is, the pressure in the air gap (α) can be released.

The releasing part 11 according to the present embodiment is a connecting part provided above the air gap (α) (in an upper part of the liquid-phase-portion case Ca). Alternatively, the releasing part 11 may be a connecting part provided below the air gap (α) (in a lower part of the gas-phase-portion case Cb) as illustrated in FIG. 12, or a connecting part provided on a lateral side of the air gap (α) (in a lateral side part of the liquid-phase-portion case Ca). Note that the releasing part 11, which is provided at only one position of the case C in the present embodiment, may be provided at each of a plurality of positions (for example, a plurality of positions aligned in the circumferential direction of the case C).

The pressure detector 10 as a medical device manufactured as above is heated at a temperature lower than or equal to the transition point or softening point of glass and is then cooled. Thus, an annealing process for removing the internal (residual) stress in the resin is performed. After the annealing process, autoclave sterilization is performed in which the pressure detector 10 is heated in saturated vapor for sterilization. Autoclave sterilization is performed in a high-pressure environment created by raising the boiling point so that the environment can have some moisture even at high temperatures. Subsequently, a drying process is performed. Thus, the pressure detector 10 as a medical device that has been wetted in autoclave sterilization is dried.

According to the present embodiment, the pressure in the air gap (α) is released through the connecting part (the releasing part 11) connecting the air gap (α) and the outside of the case C to each other. Therefore, the occurrence of excessive pressure increase in the air gap (α) can be suppressed more assuredly and smoothly. Note that the shape of the opening of the connecting part as the releasing part 11 is not limited to a circle and may be an oval, a rectangle, or any other shape.

Now, a pressure detector 10 as a medical device according to a second embodiment of the present invention will be described.

As with the case of the above embodiment, as illustrated in FIG. 1, the pressure detector 10 according to the present embodiment is connected to the venous blood circuit 2 at a position between the dialyzer 3 and the air-trap chamber 5 and is capable of detecting the pressure of the blood flowing in the venous blood circuit 2 (the blood circuit). Components that are the same as those described in the above embodiment are denoted by corresponding ones of the reference numerals, and detailed description thereof is omitted.

As with the case of the above embodiment, the releasing part 11 is provided for releasing the pressure in the air gap (α) between the sealing part Q1 and the fixing parts Q2 and Q3 when the liquid-phase-portion case Ca (the first case portion) and the gas-phase-portion case Cb (the second case portion) are fixed to each other at the fixing parts Q2 and Q3. In the present embodiment, as illustrated in FIGS. 14 to 18, the releasing part 11 is provided in the holding surface m1 or m2 of the liquid-phase-portion case Ca (the first case portion) or the gas-phase-portion case Cb (the second case portion) (in the present embodiment, as illustrated in FIG. 16, the holding surface m2 of the gas-phase-portion case Cb) and serves as a connecting groove that connects the air gap (α) and the liquid-phase portion S1 (the first housing space) or the gas-phase portion S2 (the second housing space) (in the present embodiment, the air gap (α) and the gas-phase portion S2) to each other.

When the liquid-phase-portion case Ca and the gas-phase-portion case Cb are welded (fixed) to each other at the fixing parts Q2 and Q3, as illustrated in FIGS. 14 to 16, the connecting groove as the releasing part 11 establishes a connected state (a state where the air gap (α) and the gas-phase portion S2 are connected to each other), where the connecting groove releases the pressure generated in the air gap (α) to the gas-phase portion S2. Subsequently, as illustrated in FIGS. 17 and 18, a pressing force is applied from the sealing part Q1 to the membrane member M, whereby the connecting groove is closed by the membrane member M (an elastic membrane).

According to the present embodiment, when the liquid-phase-portion case Ca and the gas-phase-portion case Cb are fixed to each other at the fixing parts Q2 and Q3, the connecting groove (the releasing part 11) provided in the holding surface m1 or m2 of the liquid-phase-portion case Ca (the first case portion) or the gas-phase-portion case Cb (the second case portion) and connecting the air gap (α) and the liquid-phase portion S1 (the first housing space) or the gas-phase portion S2 (the second housing space) to each other not only releases the pressure generated in the air gap (α) but is also closed by the membrane member M (the elastic membrane). Therefore, the occurrence of excessive pressure increase in the air gap (α) produced between the sealing part Q1 and the fixing parts Q2 and Q3 can be suppressed. Furthermore, after the pressure in the air gap (α) is released, the connecting groove (the releasing part 11) can be closed naturally.

Now, a pressure detector 10 as a medical device according to a third embodiment of the present invention will be described.

As with the case of the above embodiment, as illustrated in FIG. 1, the pressure detector 10 according to the present embodiment is connected to the venous blood circuit 2 at a position between the dialyzer 3 and the air-trap chamber 5 and is capable of detecting the pressure of the blood flowing in the venous blood circuit 2 (the blood circuit). Components that are the same as those described in the above embodiment are denoted by corresponding ones of the reference numerals, and detailed description thereof is omitted.

As with the cases of the above embodiments, the releasing part 11 is provided for releasing the pressure in the air gap (α) between the sealing part Q1 and the fixing parts Q2 and Q3 when the liquid-phase-portion case Ca (the first case portion) and the gas-phase-portion case Cb (the second case portion) are fixed to each other at the fixing parts Q2 and Q3. In the present embodiment, as illustrated in FIGS. 19 to 22, the releasing part 11 is a cut part provided in a region of the fixing part Q2 or Q3 of the liquid-phase-portion case Ca (the first case portion) or the gas-phase-portion case Cb (the second case portion) (in the present embodiment, as illustrated in FIG. 20, the fixing part Q3 of the gas-phase-portion case Cb).

As illustrated in FIG. 21, when the liquid-phase-portion case Ca and the gas-phase-portion case Cb are fixed to each other at the fixing parts Q2 and Q3, the cut part as the releasing part 11 releases the pressure generated in the air gap ($\alpha$). Subsequently, as illustrated in FIG. 22, the cut part is closed with the melting or deformation (in the present embodiment, deformation by compression) of the fixing parts Q2 and Q3 or regions therearound under the pressing force applied thereto at the time of welding. The releasing part 11 according to the present embodiment is closed after the pressure in the air gap ($\alpha$) is released. Alternatively, the releasing part 11 may be kept open instead of being closed. Note that the releasing part 11, which is provided at only one position of the case C in the present embodiment, may be provided at each of a plurality of positions (for example, a plurality of positions aligned in the circumferential direction of the case C).

According to the present embodiment, the pressure in the air gap ($\alpha$) is released through the cut part (the releasing part 11) provided in a region of the fixing part Q2 or Q3 of the liquid-phase-portion case Ca (the first case portion) or the gas-phase-portion case Cb (the second case portion). That is, the pressure in the air gap ($\alpha$) can be released from the position where the fixing part Q2 or Q3 is provided. In particular, when the liquid-phase-portion case Ca and the gas-phase-portion case Cb are fixed to each other at the fixing parts Q2 and Q3, the cut part (the releasing part 11) according to the present embodiment not only releases the pressure generated in the air gap ($\alpha$) but is also closed with the melting of the fixing parts Q2 and Q3 or regions therearound. Therefore, the occurrence of excessive pressure increase in the air gap ($\alpha$) produced between the sealing part Q1 and the fixing parts Q2 and Q3 can be suppressed. Furthermore, after the pressure in the air gap ($\alpha$) is released, the cut part can be closed naturally.

According to each of the first to third embodiments, the pressure detector 10 as a medical device includes the fixing parts Q2 and Q3 provided at the respective peripheries of the first case portion (the liquid-phase-portion case Ca) and the second case portion (the gas-phase-portion case Cb) and at which the first case portion and the second case portion that are mated to each other are fixed to each other, the holding surfaces m1 and m2 provided at the respective peripheries of the first case portion and the second case portion and between which the peripheral edge of the elastic membrane (the membrane member M) is held, and the sealing part Q1 provided at the periphery of the first case portion or the second case portion on the inner side with respect to the fixing parts Q2 and Q3 and that seals the entirety of the peripheral edge of the elastic membrane (the membrane member M) held between the holding surfaces m1 and m2. Furthermore, the pressure in the air gap ($\alpha$) produced between the sealing part Q1 and the fixing parts Q2 and Q3 is released through the releasing part 11. Therefore, the occurrence of excessive pressure increase in the air gap ($\alpha$) can be suppressed. Consequently, improvements in quality and reliability can be achieved.

In particular, according to the present embodiment, when the liquid-phase-portion case Ca (the first case portion) and the gas-phase-portion case Cb (the second case portion) are fixed to each other at the fixing parts Q2 and Q3, the pressure generated in the air gap ($\alpha$) is released. Therefore, if the pressure detector 10 as a finished medical device is subjected to autoclave sterilization, annealing, or a high-temperature environment of use, the occurrence of pressure increase in the air gap ($\alpha$) can be suppressed.

Furthermore, the case C according to the present embodiment is connectable to the flow route for liquid; the first housing space serves as the liquid-phase portion S1 to be supplied with the liquid in the flow route; the second housing space serves as the gas-phase portion S2 to be supplied with gas; the elastic membrane is the membrane member M with which the liquid-phase portion and the gas-phase portion are separated from each other and that is displaceable in accordance with the pressure of the liquid supplied into the liquid-phase portion; and the medical device serves as the pressure detector 10 that detects the pressure of the liquid in the flow route by detecting the pressure in the gas-phase portion S2. Therefore, the occurrence of excessive pressure increase in the air gap ($\alpha$) produced between the sealing part Q1 and the fixing parts Q2 and Q3 is suppressed. Consequently, the quality and reliability of the pressure detector 10 can be improved.

While some embodiments have been described above, the present invention is not limited thereto. For example, as illustrated in FIG. 23, a releasing part (11 and 12) may be employed that releases the pressure in the air gap ($\alpha$) by being bent outward or displaced under the pressure generated in the air gap ($\alpha$) when the liquid-phase-portion case Ca and the gas-phase-portion case Cb are fixed (welded) to each other at the fixing parts Q2 and Q3. Such a releasing part (11 and 12) includes a connecting part 11 that connects the air gap ($\alpha$) and the outside of the case C to each other, and a flexible component 12 as an elastic member having an elasticity higher than or equal to that of the membrane member M. When the pressure in the air gap ($\alpha$) increases, the flexible component 12 is bent outward or displaced in the connecting part 11, whereby the pressure is released.

The connecting part 11 that connects the air gap ($\alpha$) and the outside of the case C to each other may be replaced with, as illustrated in FIG. 24, a recess 11' provided in the air gap ($\alpha$). In that case, when the pressure in the air gap ($\alpha$) increases, the flexible component 12 is bent outward or displaced in the recess 11', whereby the pressure is released. Since the flexible component 12 is bent outward or displaced with the pressure change, the occurrence of excessive pressure increase in the air gap ($\alpha$) produced between the sealing part Q1 and the fixing parts Q2 and Q3 can be suppressed.

Another alternative is illustrated in FIG. 25. Specifically, the releasing part 11 serves as a connecting part that connects the air gap ($\alpha$) and the outside of the case C to each other, and a projected part 13 is provided at the edge of the opening of the connecting part. After the pressure in the air gap ($\alpha$) generated in fixing (welding) the liquid-phase-portion case Ca and the gas-phase-portion case Cb to each other at the fixing parts Q2 and Q3 is released to the outside, the projected part 13 is melted (swaged) to form a closing part 14 as illustrated in FIG. 26. Thus, the connecting part may be closed.

Yet another alternative is as follows. The releasing part 11 serves as a connecting part that connects the air gap ($\alpha$) and the outside of the case C to each other. After the pressure in the air gap ($\alpha$) generated in fixing (welding) the liquid-phase-portion case Ca and the gas-phase-portion case Cb to each other at the fixing parts Q2 and Q3 is released to the outside, the connecting part may be closed (plugged) with a separately prepared plug member 15 as illustrated in FIG. 27. In such a case, the connecting part of the pressure detector 10 as a finished medical device can be prevented from being left open. Consequently, entry of foreign substances or the like into the opening of the connecting part can be prevented.

Yet another alternative is as follows. The releasing part 11 serves as a connecting part that connects the air gap (α) and the outside of the case C to each other. After the pressure in the air gap (α) generated in fixing (welding) the liquid-phase-portion case Ca and the gas-phase-portion case Cb to each other at the fixing parts Q2 and Q3 is released to the outside, the connecting part may be closed with a separately prepared filter member 16 as illustrated in FIG. 28. In such a case, the connecting part of the pressure detector 10 as a finished medical device can be prevented from being left open. Consequently, entry of foreign substances or the like into the opening of the connecting part can be prevented. Note that the plug member 15 illustrated in FIG. 27 and the filter member 16 illustrated in FIG. 28 may each be a plate-like member that covers the outer opening of the connecting part 11.

Yet another alternative is illustrated in FIG. 29. Specifically, a closed space 17 is provided inside the membrane member M, whereby the pressure in the air gap (α) generated in fixing (welding) the liquid-phase-portion case Ca and the gas-phase-portion case Cb to each other at the fixing parts Q2 and Q3 may be released to the outside by using the closed space 17. More specifically, when the pressure in the air gap (α) increases, the volume of the closed space 17 is reduced. Thus, the pressure can be released.

On the other hand, the pressure detector 10 as a medical device is manufactured as follows. As illustrated in FIGS. 30 and 31, the liquid-phase-portion case Ca (the first case portion) and the gas-phase-portion case Cb (the second case portion) that are mated to each other are fixedly set on a jig R, and the entirety of the peripheral edge of the membrane member M (the elastic membrane) that is held between the holding surfaces m1 and m2 is sealed. The jig R may have a jig releasing part Ra that releases the pressure in the air gap (α) produced between the sealing part Q1 and the fixing parts Q2 and Q3. The jig releasing part Ra is a passage provided in the jig R and connects the connecting part 11 and the outside to each other, thereby releasing the pressure. The drawings illustrates a state where the liquid-phase-portion case Ca is placed on the jig R with the gas-phase-portion case Cb mated thereto from above. Alternatively, the gas-phase-portion case Cb may be placed on the jig R with the liquid-phase-portion case Ca mated thereto from above.

In the above manufacturing process, the pressure in the air gap (α) can be released more assuredly without being accumulated therein. Furthermore, the occurrence of relative displacement between the liquid-phase-portion case Ca (the first case portion) and the gas-phase-portion case Cb (the second case portion) can be suppressed. Consequently, the liquid-phase-portion case Ca and the gas-phase-portion case Cb can be fixed to each other accurately. In particular, the above jig R may be employed in a case where the fixing parts Q2 and Q3 are melted to be bonded to each other by ultrasonic welding or laser welding. In such a case, since air in the air gap (α) can be released to the outside through the jig releasing part Ra, molten resin can be prevented from flowing into a gap (β) between the liquid-phase-portion case Ca and the gas-phase-portion case Cb (a gap, illustrated in FIG. 31, produced when the liquid-phase-portion case Ca and the gas-phase-portion case Cb are mated to each other) and forming burrs.

The connecting part 11 may be provided at each of a plurality of positions aligned in the circumferential direction of the case C. For example, as illustrated in FIGS. 32 and 33, a plurality of connecting parts 11 each having a circular opening may be aligned in the circumferential direction of the liquid-phase-portion case Ca (or the gas-phase-portion case Cb, or each of the liquid-phase-portion case Ca and the gas-phase-portion case Cb). As another example, as illustrated in FIGS. 34 and 35, a plurality of connecting parts 11 each having a rectangular opening may be aligned in the circumferential direction of the liquid-phase-portion case Ca (or the gas-phase-portion case Cb, or each of the liquid-phase-portion case Ca and the gas-phase-portion case Cb). In particular, in the example illustrated in FIGS. 34 and 35, since a grid pattern is formed as a whole, the strength of the case C can be maintained.

The releasing part 11 according to each of the above embodiments releases the pressure in the air gap (α) when the liquid-phase-portion case Ca (the first case portion) and the gas-phase-portion case Cb (the second case portion) are fixed (welded) to each other at the fixing parts Q2 and Q3. Alternatively, the releasing part 11 may release the pressure in the air gap (α) at another timing, such as the timing when annealing is performed, when autoclave sterilization is performed, or when used in a high-temperature environment, instead of the timing when the liquid-phase-portion case Ca and the gas-phase-portion case Cb are fixed (welded) to each other.

In each of the embodiments, the liquid-phase-portion case Ca (the first case portion) and the gas-phase-portion case Cb (the second case portion) are welded to each other by melting the fixing parts Q2 and Q3 with an ultrasonic wave, and the pressure generated in the air gap (α) in the welding process is released through the releasing part 11. Alternatively, the releasing of the pressure in the air gap (α) is not limited to be performed in ultrasonic welding and may be performed in another fixing process (such as laser welding, or an assembling process of press-fitting or screwing).

The pressure detector 10 according to each of the embodiments is connected to a position of the venous blood circuit 2 that is between the dialyzer 3 and the air-trap chamber 5. Alternatively, the pressure detector 10 may be connected to another position of the blood circuit (for example, a position of the arterial blood circuit 1 that is between the distal end and the blood pump 4, or a position of the arterial blood circuit 1 that is between the blood pump 4 and the dialyzer 3). The blood circuit to which the present pressure detector 10 is to be connected may be of another type. For example, the blood circuit may be provided with the present pressure detector 10 instead of the air-trap chamber 5.

The liquid-phase-portion case Ca is not limited to the one having two ports serving as the inlet port C1 and the outlet port C2 as in each of the above embodiments. For example, the liquid-phase-portion case Ca may be the one having a single port C4 as illustrated in FIGS. 36 and 37, or the one having five ports (C5 to C9) as illustrated in FIGS. 38 and 39. In the example illustrated in FIGS. 38 and 39, the number of ports to be provided to the liquid-phase-portion case Ca is not limited to five and may be four, six, or seven or more.

The embodiments each concern the pressure detector 10 provided to a blood circuit intended for dialysis treatment. Alternatively, the present invention may be applied to another medical device (such as a diaphragm pump) including a case obtained by mating a first case portion and a second case portion to each other, the case having a housing space inside; an elastic membrane as an elastic member attached to the case and with which a first housing space covered by the first case portion and a second housing space covered by the second case portion are separated from each other; fixing parts provided at the respective peripheries of the first case portion and the second case portion and at which the first case portion and the second case portion that are mated to each other are fixed to each other; holding surfaces provided at the respective peripheries of the first case portion and the second case portion and between which the peripheral edge of the elastic membrane is held; and a sealing part provided at the periphery of the first case portion or the second case portion on the inner side with respect to the fixing parts and that seals the entirety of the peripheral edge of the elastic membrane held between the holding surfaces.

For example, if the one illustrated in FIGS. 36 and 37 is used as a diaphragm pump, the following configuration may be employed: an air pump 20 and a pressure sensor 21 are connected to the connection port C3, the port C4 is connected to the flow route for liquid, and a valve Va and a valve Vb are provided to the upstream side and the downstream side, respectively, of the flow route, whereby the diaphragm pump is controlled. In such a case, when the air pump 20 is activated with the valve Va open and the valve Vb closed, the membrane member M is attracted toward the wall of the gas-phase-portion case Cb (the second case portion). Thus, the liquid can be introduced into the liquid-phase-portion case Ca. On the other hand, when the air pump 20 is activated reversely with the valve Va closed and the valve Vb open, the membrane member M is attracted toward the wall of the liquid-phase-portion case Ca (the first case portion). Thus, the liquid in the liquid-phase-portion case Ca can be discharged. With the repetition of the above activation of the air pump 20 and operation of the valves Va and Vb, the medical device can function as a diaphragm pump. The above drawings illustrate a case where the pressure sensor 21 is capable of detecting the attraction of the membrane member M to the wall of the liquid-phase-portion case Ca (the first case portion) or the gas-phase-portion case Cb (the second case portion). Alternatively, such a pressure sensor 21 may be omitted.

As another example, if the one illustrated in FIGS. 38 and 39 is used as a diaphragm pump, the following configuration may be employed: an air pump 20 and a pressure sensor 21 are connected to the connection port C3, the ports C5 to C9 are connected to respective flow routes for liquid, and valves V1 to V5 are provided to the respective flow routes, whereby the diaphragm pump is controlled. In such a case, when the air pump 20 is activated with the valve V1 open and the other valves V2 to V5 closed, the membrane member M is attracted toward the wall of the gas-phase-portion case Cb (the second case portion). Thus, the liquid can be introduced into the liquid-phase-portion case Ca. On the other hand, when the air pump 20 is activated reversely with the valve V1 closed and the other valves V2 to V5 open, the membrane member M is attracted toward the wall of the liquid-phase-portion case Ca (the first case portion). Thus, the liquid in the liquid-phase-portion case Ca can be discharged. With the repetition of the above activation of the air pump 20 and operation of the valves V1 to V5, the medical device can function as a diaphragm pump. The above drawings illustrate a case where the pressure sensor 21 is capable of detecting the attraction of the membrane member M to the wall of the liquid-phase-portion case Ca (the first case portion) or the gas-phase-portion case Cb (the second case portion). Alternatively, such a pressure sensor 21 may be omitted.

In the above embodiment, the port C5 serves as an inlet port for taking in the liquid, and the other ports (C6 to C9) each serve as an outlet port for discharging the liquid. The timing of opening/closing the valves V1 to V5 may be changed arbitrarily, whereby the combination of inlet ports and outlet ports can be changed correspondingly. Specifically, if the membrane member M is attracted toward the wall of the gas-phase-portion case Cb (the second case portion), any (not limited to one and any are selectable) of the ports of the flow routes that are opened by corresponding ones of the valves V1 to V5 each serve as an inlet port. If the membrane member M is attracted toward the wall of the liquid-phase-portion case Ca (the first case portion), any (not limited to one and any are selectable) of the ports of the flow routes that are opened by corresponding ones of the valves V1 to V5 each serve as an inlet port.

The present invention is applicable to any medical device and any method of manufacturing the same in any other mode or for any other use, as long as a releasing part that releases the pressure in an air gap produced between a fixing part and a sealing part is provided.

REFERENCE SIGN LIST 1 arterial blood circuit
2 venous blood circuit
3 dialyzer (blood purifier)
4 blood pump
5 air-trap chamber
6 dialysis device
7 storage unit
8 air-trap chamber
9 clamp unit
10 pressure detector (medical device)
11 releasing part
12 releasing part
13 projected part
14 closing part
15 plug member
16 filter member
17 closed space
L1 dialysate introduction line
L2 dialysate drain line
L3 physiological-saline supply line
C case
Ca liquid-phase-portion case (first case portion)
Ca1 inlet opening
Ca2 outlet opening
Cb gas-phase-portion case (second case portion)
Cb1 opening
Cb2 rib
Cb3 ridge
Cb4 recess
C1 inlet port
C1a flow-route portion
C1b connecting portion
C2 outlet port
C2a flow-route portion
C2b connecting portion
C3 connection port
M membrane member (elastic membrane)
Ma periphery
P pressure detection sensor (pressure-detecting unit)
S1 liquid-phase portion (first housing space)
S2 gas-phase portion (second housing space)
K pipe
Q1 sealing part
Q2, Q3 fixing part
m1, m2 holding surface
(α) air gap R jig
Ra jig releasing part

The invention claimed is:

1. A medical device comprising:
a case obtained by mating a first case portion and a second case portion to each other, the case having a housing space inside;
an elastic membrane as an elastic member attached to the case and with which a first housing space covered by the first case portion and a second housing space covered by the second case portion are separated from each other;
fixing parts provided at respective peripheries of the first case portion and the second case portion and at which the first case portion and the second case portion that are mated to each other are fixed to each other by melting;
holding surfaces provided at the respective peripheries of the first case portion and the second case portion and between which a peripheral edge of the elastic membrane is held;
a sealing part provided at the periphery of the first case portion or the second case portion on an inner side with respect to the fixing parts and that seals an entirety of the peripheral edge of the elastic membrane held between the holding surfaces and
a releasing part that releases a pressure in an air gap that is located between the case and the elastic membrane and extends between the sealing part and the fixing parts wherein the releasing part serves as a cut part provided in a region of the fixing part of the first case portion or the second case portion, and when the first case portion and the second case portion are fixed to each other at the fixing parts,
wherein the cut part releases the pressure generated in the air gap and the cut part is closed by melting of the fixing parts or regions around the fixing parts; and
wherein the fixing parts are annularly formed in the first case portion and the second case portion, and the cut part extends in a radial direction in the fixing parts of the first case portion and the second case portion.

2. The medical device according to claim 1, wherein when the first case portion and the second case portion are fixed to each other at the fixing parts, the releasing part releases the pressure generated in the air gap.

3. The medical device according to claim 1, wherein the case is connectable to a flow route for liquid; the first housing space serves as a liquid-phase portion to be supplied with the liquid in the flow route; the second housing space serves as a gas-phase portion to be supplied with gas; the elastic membrane is a membrane member with which the liquid-phase portion and the gas-phase portion are separated from each other and that is displaceable in accordance with a pressure of the liquid supplied into the liquid-phase portion; and the medical device serves as a pressure detector that detects the pressure of the liquid in the flow route by detecting a pressure in the gas-phase portion.

4. The medical device according to claim 1, wherein when the first case portion and the second case portion are fixed to each other at the fixing parts, the releasing part releases the pressure in the air gap by being bent outward or displaced under the pressure generated in the air gap.

5. The medical device according to claim 1, wherein the air gap extends through the cut part so that the pressure extends through the cut part.

* * * * *